(12) United States Patent
Ozer et al.

(10) Patent No.: US 11,691,946 B2
(45) Date of Patent: Jul. 4, 2023

(54) PREPARATION OF TRIFAROTENE AND INTERMEDIATES AND POLYMORPHS THEREOF

(71) Applicant: TARO PHARMACEUTICAL INDUSTRIES LTD., Haifa Bay (IL)

(72) Inventors: Ilana Ozer, Yokneam (IL); Yulia Kaftanov, Haifa (IL); Elliot Simhon, Haifa (IL); Andrey Dushkin, Haifa (IL); Shani Sheffer Dee-Noor, Haifa (IL); Hillel Pizem, Netanya (IL); Avi Avramoff, Haifa (IL)

(73) Assignee: TARO PHARMACEUTICAL INDUSTRIES LTD., Haifa Bay (IL)

( * ) Notice: Subject to any disclaimer, the term of this patent is extended or adjusted under 35 U.S.C. 154(b) by 0 days.

(21) Appl. No.: 17/756,994

(22) PCT Filed: Dec. 10, 2020

(86) PCT No.: PCT/US2020/064365
§ 371 (c)(1),
(2) Date: Jun. 7, 2022

(87) PCT Pub. No.: WO2021/119351
PCT Pub. Date: Jun. 17, 2021

(65) Prior Publication Data
US 2023/0051259 A1    Feb. 16, 2023

Related U.S. Application Data

(60) Provisional application No. 62/946,943, filed on Dec. 11, 2019.

(51) Int. Cl.
*C07D 207/08*     (2006.01)

(52) U.S. Cl.
CPC ........ *C07D 207/08* (2013.01); *C07B 2200/13* (2013.01)

(58) Field of Classification Search
CPC .................................................. C07D 207/08
See application file for complete search history.

(56) References Cited

U.S. PATENT DOCUMENTS

| 2006/0264629 A1 | 11/2006 | He et al. |
| 2010/0184739 A1 | 7/2010 | Sheth et al. |

FOREIGN PATENT DOCUMENTS

WO    2006/066978 A1    6/2006

OTHER PUBLICATIONS

International Search Report dated May 28, 2021 in corresponding International Patent Application No. PCT/US2020/064365.
Liu et al., "Fluoro, Alkylsulfanyl, and Alkylsulfonyl Leaving Groups in Suzuki Cross-Coupling Reactions of Purine 2'-Deoxynucleosides and Nucleosides," Org Lett 7(6):1149-1151 (2005).
El-Berjawi et al., "Synthesis of a perylenediimide-fullerene C60 dyad: A simple use of a nitro leaving group for a Suzuki-Miyaura coupling reaction," Dyes Pigments 159:551-556 (2018).
Chemler et al., "The B-Alkyl Suzuki-Miyaura Cross-Coupling Reaction: Development, Mechanistic Study, and Applications in Natural Product Synthesis," Angew Chem Int Ed 40(24):4544-4568 (2001).
Nun et al., "Solvent-free microwave-assisted Suzuki-Miyaura coupling catalyzed by PEPPSI-iPr," Synlett 11:1761-1764 (2009).
Tasker et al., "Recent advances in nickel catalysis," Nature 509(7500):299-309 (2014).
Yang et al., "Copper-Catalyzed Cross-Coupling Reaction of Organoboron Compounds with Primary Alkyl Halides and Pseudohalides," Angew Chem Int Ed Engl 50(17):3904-3907 (2011).
Barder et al., "Catalysts for Suzuki-Miyaura coupling processes: scope and studies of the effect of ligand structure," J Am Chem Soc 127(13):4685-4696 (2005).
Bedford et al., "Simple mixed Fe—Zn catalysts for the Suzuki couplings of tetraarylborates with benzyl halides and 2-halopyridines," Chem Commun (Camb) 42:6430-6432 (2009).
Martin et al., "Palladium-Catalyzed Suzuki-Miyaura Cross-Coupling Reactions Employing Dialkylbiaryl Phosphine Ligands," Acc Chem Res 41(11):1461-1473 (2008).
Kuwano et al., "Suzuki-Miyaura Cross-Coupling of Benzylic Carbonates with Arylboronic Acids," Org Lett 7:945 (2005).
Tao et al., "Simple Amine/Pd(OAc)2-Catalyzed Suzuki Coupling Reactions of Aryl Bromides under Mild Aerobic Conditions," J Org Chem 69:4330 (2004).
Suzuki, "Recent advances in the cross-coupling reactions of organoboron derivatives with organic electrophiles, 1995-1998," J Organometallic Chem 576:147-168 (1999).
Miyaura et al., "Palladium-catalyzed cross-coupling reactions of organoboron compounds," Chem Rev 95:2457-2483 (1995).

(Continued)

*Primary Examiner* — Rebecca L Anderson
(74) *Attorney, Agent, or Firm* — Medler Ferro Woodhouse & Mills PLLC

(57) ABSTRACT

The present disclosure provides a process for the preparation of Trifarotene. The disclosure also provides novel intermediates in the process described herein. Also provided are novel polymorphs of Trifarotene.

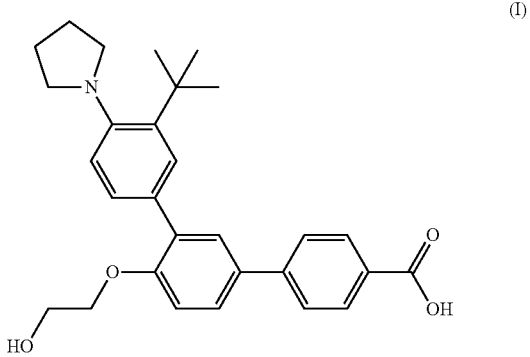

(I)

20 Claims, 9 Drawing Sheets

(56) References Cited

OTHER PUBLICATIONS

Paul et al., "Suzuki-Miyaura reaction by heterogeneously supported Pd in water: Recent studies," RSC Adv 5:42193 (2015).
Suzuki, "Organoborane coupling reactions (Suzuki coupling)," Proc Jpn Acad, Ser B. 80(8):359 (2004).

PREPARATION OF TRIFAROTENE AND INTERMEDIATES AND POLYMORPHS THEREOF

FIELD OF THE INVENTION

The present disclosure provides a process for the preparation of Trifarotene. The disclosure also provides novel intermediates in the process described herein. Also provided are novel polymorphs of Trifarotene.

BACKGROUND

3"-(tert-butyl)-4'-(2-hydroxyethoxy)-4"-(pyrrolidin-1-yl)-[1,1':3',1"-terphenyl]-4-carboxylic acid, commonly known as Trifarotene, is a topical retinoid that can selectively target retinoic acid receptor (RAR) gamma, the most common RAR found in the skin. Trifarotene is prescribed for treatment of acne vulgaris and was first approved in the United States in October 2019. Current synthetic routes for Trifarotene, e.g., described in WO 2006/066978, include several challenging steps, e.g., performing a reaction at −78° C. and using two separate protecting groups that must be hydrolyzed under different conditions, which can decrease workflow efficiency and overall yield.

SUMMARY OF THE INVENTION

In some embodiments, the disclosure provides a process for the preparation of a compound of Formula (I) [Trifarotene], or a salt thereof

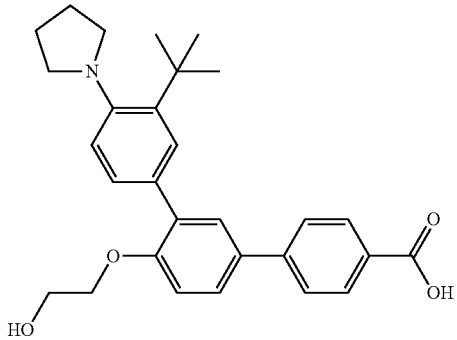

(I)

comprising hydrolyzing a compound of Formula (V)

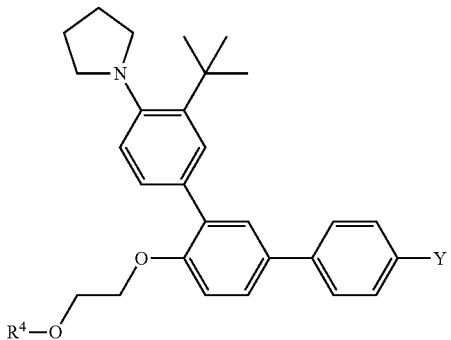

(V)

wherein $R^4$ is hydrogen, a substituted or unsubstituted linear or branched $C_1$-$C_8$ alkanoyl group, a substituted or unsubstituted linear or branched $C_1$-$C_8$ alkenoyl group, a substituted or unsubstituted linear or branched $C_1$-$C_8$ alkynoyl group, a substituted or unsubstituted cycloalkanoyl group, a substituted or unsubstituted aryl carbonyl group, a substituted or unsubstituted heterocyle carbonyl group, a substituted or unsubstituted heteroaryl carbonyl group, or a $C_1$-$C_8$ alkanoyl group comprising a heteroatom; and wherein Y is a nitrile (CN) or amide ($CONH_2$); to obtain the compound of Formula (I). In some embodiments, $R^4$ is an acetyl group. In some embodiments, $R^4$ is hydrogen.

In some embodiments, the process further comprises preparing the compound of formula (V) by hydrolyzing a compound of Formula (IV)

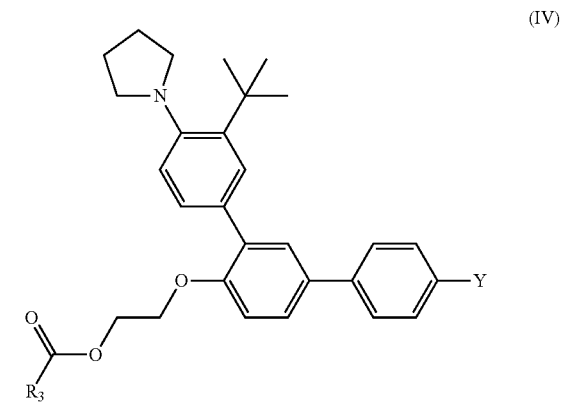

(IV)

in the presence of a base, wherein $R^3$ is hydrogen, a hydroxyl group, a halogen, a substituted or unsubstituted linear or branched $C_1$-$C_8$ alkyl group, a substituted or unsubstituted linear or branched $C_1$-$C_8$ alkenyl group, a substituted or unsubstituted linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; and wherein Y is a nitrile (CN) or amide ($CONH_2$); to obtain the compound of formula (V). In some embodiments, $R^3$ is methyl.

In some embodiments, the hydrolysis is performed in the presence of a solvent comprising water, methanol (MeOH), ethanol (EtOH), propanol (PrOH), isopropanol (IPA), or any mixture thereof. In some embodiments, the solvent comprises water and ethanol. In some embodiments, the base comprises sodium hydroxide (NaOH), potassium hydroxide (KOH), lithium hydroxide (LiOH), barium hydroxide (Ba(OH)$_2$), or any mixture thereof.

In some embodiments, the compound of formula (IV) is present in an amount of about 0.01 to about 0.5 mol/L (solvent), preferably about 0.02 to about 0.2 mol/L (solvent), more preferably about 0.04 to about 0.08 mol/L (solvent). In some embodiments, the base is present in an amount of about 0.1 to about 1 mol/L (solvent), preferably about 0.2 to about 0.8 mol/L (solvent), more preferably about 0.3 to about 0.6 mol/L (solvent). In some embodiments, the base is present at about 1 to about 10 molar equivalents relative to the compound of formula (IV), preferably about 2 to about 8 molar equivalents relative to the compound of formula (IV), more preferably about 3 to about 6 molar equivalents relative to the compound of formula (IV).

In some embodiments, the process further comprises preparing the compound of formula (IV) by reacting a compound of formula (II)

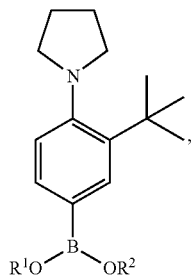

(II)

wherein $R^1$ and $R^2$ are independently hydrogen or a linear or branched $C_1$-$C_3$ alkyl, wherein $R^1$ and $R^2$ can be the same or different; or $R^1$ and $R^2$ together form a pinacolate, with a compound of formula (III)

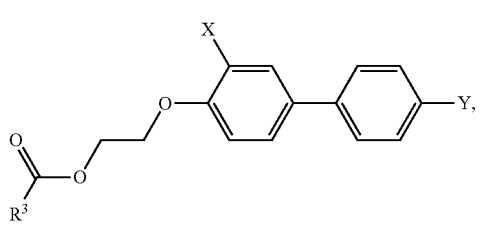

(III)

in the presence of a catalyst, wherein $R^3$ is hydrogen, a hydroxyl group, a halogen, a substituted or unsubstituted linear or branched $C_1$-$C_8$ alkyl, a substituted or unsubstituted linear or branched $C_1$-$C_8$ alkenyl group, a substituted or unsubstituted linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; wherein X is a halogen or triflate; and wherein Y is a nitrile or amide, to obtain the compound of formula (IV). In some embodiments, the $R^3$ is methyl and X is iodine.

In some embodiments, the reaction is performed in the presence of a solvent comprising toluene, dimethylformamide (DMF), dimethyl sulfoxide (DMSO), tetrahydrofuran (THF), dioxane, n-butanol (n-BuOH), isopropanol (IPA), dimethyl ether (DME), diethyl ether, or any mixture thereof. In some embodiments, the reaction is performed in the presence of a base comprising $K_2CO_3$, $CH_3CO_2K$, $K_3PO_4$, KOtBu, $Na_2CO_3$, $NaHCO_3$, NaOMe, $Cs_2CO_3$, $Ag_3PO_4$, $Ag_2O$, $Tl_2CO_3$, TlOEt, TlOH, t-BuNH$_2$, KOH, NaOH, LiOH, Ba(OH)$_2$, or combination thereof.

In some embodiments, the catalyst comprises a metal selected from Pd, Cu, or Ni. In some embodiments, the catalyst comprises at least two atoms of the metal. In some embodiments, the catalyst is a Pd catalyst selected from Pd(PPh$_3$)$_2$Cl$_2$ [bis(triphenylphosphine)palladium(II) dichloride]; Pd(PPh$_3$)$_4$ [tetrakis(triphenylphosphine)palladium (0)]; Pd(OAc)$_2$ [palladium(II) diacetate]; XPhos Pd-G3 [(2-dicyclohexylphosphino-2',4',6'-triisopropyl-1,1'-biphenyl)[2-(2'-amino-1,1'-biphenyl)]palladium(II) methanesulfonate]; SPhos-Pd-G2 [chloro(2-dicyclohexylphosphino-2',6'-dimethoxy-1,1'-biphenyl)[2-(2'-amino-1,1'-biphenyl)]palladium(II)]; CATACXIUM® A Pd G3 (mesylate[(di(1-adamantyl)-n-butylphosphine)-2-(2'-amino-1,1'-biphenyl)] palladium(II) or [(di(1-adamantyl)-butylphosphine)-2-(2'-amino-1,1'-biphenyl)]palladium(II) methanesulfonate); APhos Pd G3 (palladium G3-(4-(N,N-dimethylamino)phenyl)di-tert-butylphosphine] or [4-(di-tert-butylphosphino)-N,N-dimethylaniline-2-(2'-aminobiphenyl)]palladium(II) methanesulfonate); P(Cy$_3$) Pd-G3 (palladium G3-tricyclohexylphosphine or [(tricyclohexylphosphine)-2-(2'-aminobiphenyl)]palladium(II) methanesulfonate); Allylpalladium (II) chloride dimer (bis(allyl)dichlorodipalladium); or Pd(dppf)Cl$_2$ [1,1'-Bis(diphenylphosphino)ferrocene]dichloropalladium(II)].

In some embodiments, the compounds of formula (II) and formula (III) are present in a molar ratio of about 1:10 to about 10:1, preferably about 1:5 to about 5:1, more preferably about 1:1. In some embodiments, the compounds of formula (II) and formula (III) are independently present in an amount of about 0.01 to about 1 mol/L (solvent), preferably about 0.05 to about 0.5 mol/L (solvent), more preferably about 0.1 to about 0.4 mol/L (solvent).

In some embodiments, the catalyst is present at about 0.001 to about 1 molar equivalents relative to the compounds of formula (II) or formula (III), preferably about 0.002 to about 0.5 molar equivalents relative to the compounds of formula (II) or formula (III), more preferably about 0.003 to about 0.1 molar equivalents relative to the compounds of formula (II) or formula (III). In some embodiments, the base is present at about 0.1 to about 10 molar equivalents relative to the compounds of formula (II) or formula (III), preferably about 1 to about 6 molar equivalents relative to the compounds of formula (II) or formula (III), more preferably about 2 to about 4 molar equivalents relative to the compounds of formula (II) or formula (III).

In some embodiments, the present disclosure provides a process for the preparation of a compound of formula (I) [Trifarotene], or a salt thereof

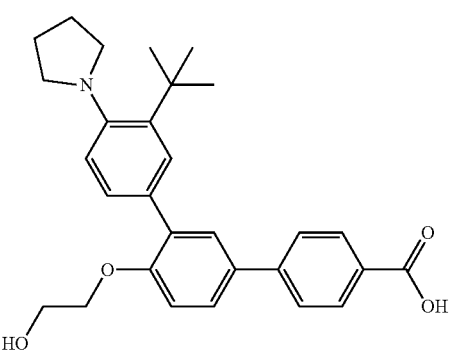

(I)

comprising reacting a compound of formula (II)

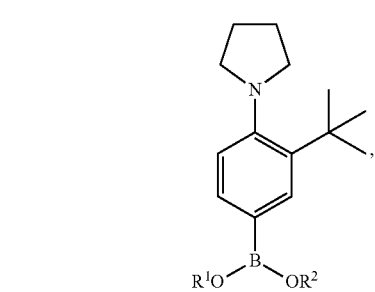

(II)

wherein $R^1$ and $R^2$ are independently hydrogen or a linear or branched $C_1$-$C_3$ alkyl, wherein $R^1$ and $R^2$ can be the same or different; or $R^1$ and $R^2$ together form a pinacolate, with a compound of formula (III)

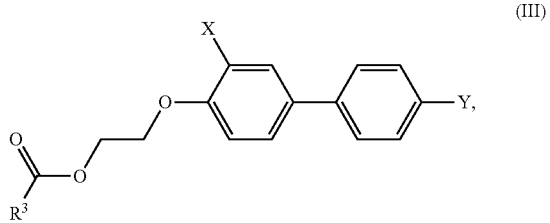

(III)

wherein R³ is a substituted or unsubstituted linear or branched C₁-C₈ alkyl, a substituted or unsubstituted linear or branched C₁-C₈ alkenyl group, a substituted or unsubstituted linear or branched C₁-C₈ alkynyl group, a substituted or unsubstituted cycloalkyl group, a substituted or unsubstituted aryl group, a substituted or unsubstituted heterocycle, a substituted or unsubstituted heteroaryl, or a C₁-C₈ alkyl group comprising a heteroatom; wherein X is a halogen or triflate; and wherein Y is a nitrile (CN) or amide (CONH₂), in the presence of a catalyst, to obtain a compound of formula (IV)

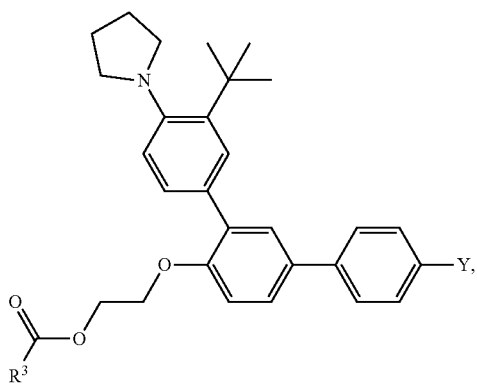

(IV)

wherein R³ is as defined above; and hydrolyzing the compound of formula (IV) in the presence of a base, to obtain Trifarotene. R¹, R², R³, R⁴, X, and Y, and the various reactions and conditions are further described herein. In some embodiments, R³ is methyl, X is iodine, and Y is nitrile. In some embodiments, R³ is methyl and X is iodine.

In some embodiments, the present disclosure provides a compound of Formula (III)

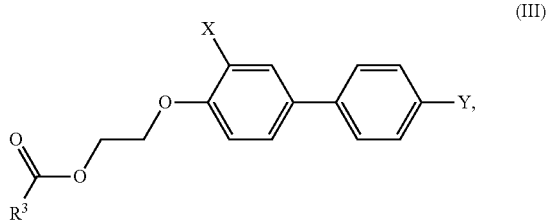

(III)

wherein R³ is a substituted or unsubstituted linear or branched C₁-C₈ alkyl group, substituted or unsubstituted linear or branched C₁-C₈ alkenyl group, substituted or unsubstituted linear or branched C₁-C₈ alkynyl group, a substituted or unsubstituted cycloalkyl group, a substituted or unsubstituted aryl group, a substituted or unsubstituted heterocycle, a substituted or unsubstituted heteroaryl, or a C₁-C₈ alkyl group comprising a heteroatom; wherein X is a halogen or triflate; and wherein Y is a nitrile or amide. In some embodiments, R³ is methyl and X is iodine.

In some embodiments, the present disclosure provides a compound of Formula (V)

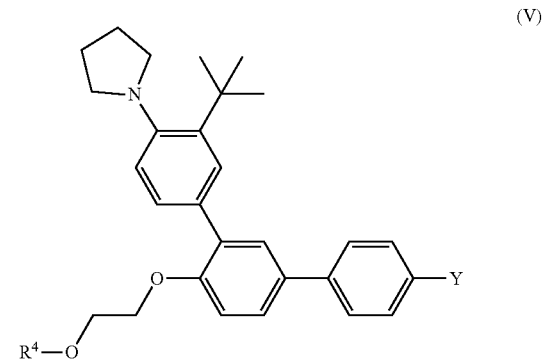

(V)

wherein R⁴ is hydrogen, a substituted or unsubstituted linear or branched C₁-C₈ alkanoyl group, a substituted or unsubstituted linear or branched C₁-C₈ alkenoyl group, a substituted or unsubstituted linear or branched C₁-C₈ alkynoyl group, a substituted or unsubstituted cycloalkanoyl group, a substituted or unsubstituted aryl carbonyl group, a substitute or unsubstituted heterocyle carbonyl group, a substituted or unsubstituted heteroaryl carbonyl group, or a C₁-C₈ alkanoyl group comprising a heteroatom; and wherein Y is a nitrile (CN) or amide (CONH₂); and wherein Y is nitrile or amide. In some embodiments, R⁴ is hydrogen. In some embodiments, R⁴ is acetyl.

In some embodiments, the disclosure provides a Form A polymorph of the compound of Formula (I) [Trifarotene-HCl], wherein the Form A polymorph shows an X-ray powder diffraction (XRPD) pattern having characteristic peaks at reflection angle 2θ of 7.6, 11.5, 15.4, 21.1, and 23.2 degrees. In some embodiments, the Form A polymorph further shows peaks at peaks at 8.6, 9.0, 17.7, 18.3, 19.5, and 22.5 degrees.

In some embodiments, the disclosure provides a Form B polymorph of the compound of Formula (I) [Trifarotene-HCl], wherein the Form B polymorph shows an X-ray powder diffraction pattern having characteristic peaks at reflection angle 2θ of 12.6, 19.5, 19.8, 24.6, and 29.5 degrees. In some embodiments, the Form B polymorph further shows peaks at 8.4, 12.0, 17.4, 21.1, 23.2, 31.0, and 32.1 degrees.

In some embodiments, the disclosure provides a Form C polymorph of the compound of Formula (I) [Trifarotene-HCl], wherein the Form C polymorph shows an X-ray powder diffraction pattern having characteristic peaks at reflection angle 2θ of 7.9, 15.6, 20.0, 23.6, and 27.8 degrees. In some embodiments, the Form C polymorph further shows peaks at 12.1, 16.4, 17.4, and 28.8 degrees.

In some embodiments, the disclosure provides a Form D polymorph of the compound of Formula (I) [Trifarotene], wherein the Form D polymorph shows an X-ray powder diffraction pattern having characteristic peaks at reflection angle 2θ of 8.5, 16.2, 18.6, and 23.1 degrees. In some embodiments, the Form D polymorph further shows peaks at 12.2, 12.8, and 14.1 degrees.

In some embodiments, the disclosure provides a Form E polymorph of the compound of Formula (I) [Trifarotene], wherein the Form E polymorph shows an X-ray powder diffraction pattern having characteristic peaks at reflection angle 2θ of 8.6, 12.8, 14.2, 17.9, and 24.0 degrees. In some embodiments, the Form E polymorph further shows peaks at 10.6, 15.3, 16.3, 19.3, and 22.0 degrees.

In some embodiments, the disclosure provides a Form F polymorph of the compound of Formula (I) [Trifarotene], wherein the Form F polymorph shows an X-ray powder diffraction pattern having characteristic peaks at reflection angle 2θ of 5.2, 6.3, 14.9, 18.0, and 19.1 degrees. In some embodiments, the Form F polymorph further shows peaks at 8.5, 15.6, 16.3, 18.5, and 22.9 degrees.

In some embodiments, the disclosure provides a Form G polymorph of the compound of Formula (I) [Trifarotene Na salt], wherein the Form G polymorph shows an X-ray powder diffraction pattern having characteristic peaks at reflection angle 2θ of 10.6, 11.5, 17.4, and 19.7 degrees. In some embodiments, the Form G polymorph further shows peaks at 8.9, 10.0, 14.7, and 16.2 degrees.

In some embodiments, the disclosure provides a process for preparing a Form A polymorph of Trifarotene-HCl, comprising: (a) providing trifarotene according to a process described herein; (b) adjusting pH of the trifarotene to a pH of about 2 to about 4, to obtain a trifarotene salt; and (c) suspending the trifarotene salt in methyl ethyl ketone, to obtain a Form A polymorph of trifarotene. In some embodiments, the pH is adjusted using HCl.

In some embodiments, the disclosure provides a process for preparing a Form B polymorph of Trifarotene-HCl, comprising: (a) providing trifarotene according to a process described herein; (b) adjusting pH of the trifarotene to a pH of about 2 to about 4, to obtain a trifarotene salt; and (c) suspending the trifarotene salt in a solvent comprising acetonitrile, ethyl acetate, tetrahydrofuran, 1-butanol; or dissolving the trifarotene salt in methanol, to obtain a Form B polymorph of trifarotene. In some embodiments, the pH is adjusted using HCl.

In some embodiments, the disclosure further provides a process for preparing a Form C polymorph of Trifarotene-HCl, comprising: providing trifarotene according to a process described herein; (b) adjusting pH of the trifarotene to a pH of about 2 to about 4, to obtain a trifarotene salt; and (c) suspending the trifarotene salt in ethylene glycol, to obtain a Form C polymorph of trifarotene. In some embodiments, the pH is adjusted using HCl.

In some embodiments, the disclosure further provides a process for preparing a Form D polymorph of Trifarotene, comprising: (a) providing trifarotene according to a process described herein; and (b) adjusting pH of the trifarotene to a pH of about 5 to about 6, to obtain a Form D polymorph of trifarotene. In some embodiments, the pH is adjusted using HCl, acetic acid, sulfuric acid, phosphoric acid, nitric acid, hydrobromic acid, trifluoroacetic acid, p-toluene sulfonic acid, methane-sulfonic acid, or any mixture thereof.

In some embodiments, the disclosure further provides a process for preparing a Form E polymorph of Trifarotene, comprising: (a) providing trifarotene according to a process described herein; (b) adjusting pH of the trifarotene to a pH of about 5 to about 6, to obtain trifarotene; and (c) suspending the trifarotene in methanol, to obtain a Form E polymorph of trifarotene.

In some embodiments, the disclosure further provides a process for preparing a Form F polymorph of Trifarotene, comprising: (a) providing trifarotene according to a process described herein; (b) adjusting pH of the trifarotene to a pH of about 5 to about 6, to obtain trifarotene; and (c) dissolving the trifarotene in isopropanol, to obtain a Form F polymorph of trifarotene.

In some embodiments, the disclosure further provides a process for preparing a Form G polymorph of Trifarotene Na salt, comprising: (a) providing trifarotene according to a process of described herein; and (b) adjusting pH of the trifarotene to a pH of about 9 to about 12, to obtain a Form G polymorph of trifarotene. In some embodiments, the pH is adjusted using sodium hydroxide.

DETAILED DESCRIPTION OF THE INVENTION

Figure 1:
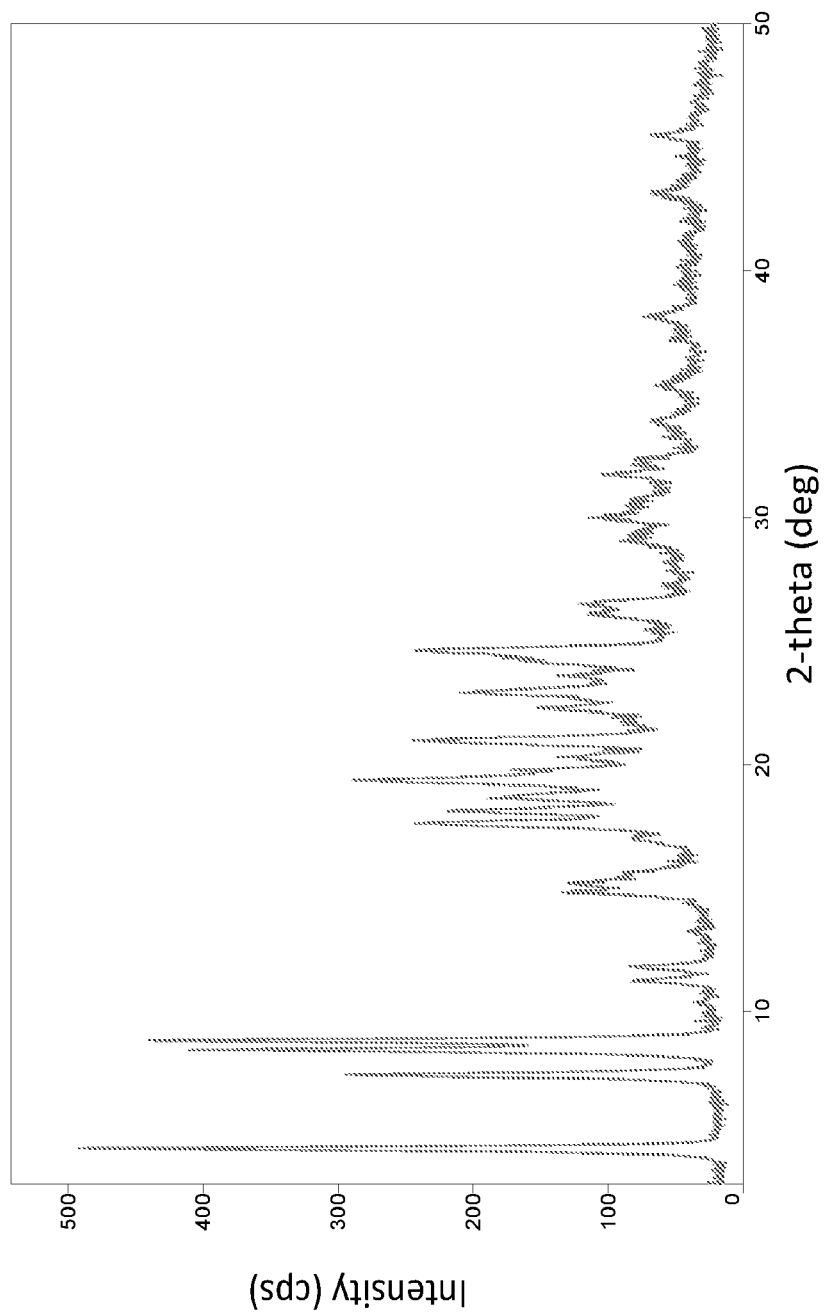
FIG. 1 shows an X-ray powder diffraction (XRPD) spectra of Trifarotene HCl salt as described in embodiments herein.

The present disclosure relates to methods for the preparation of Trifarotene. The methods provided herein advantageously simplify the preparation process by reducing or eliminating reaction steps that require harsh conditions (e.g., performed in extreme heat (e.g., >50° C.) or cold (e.g., <−10° C.)).

As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% or higher variability, depending on the situation. In some embodiments, one of skill in the art will understand the level of variability indicated by the term "about," due to the context in which it is used herein. It should also be understood that use of the term "about" also includes the specifically recited value.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited elements or method steps. It is contemplated that any embodiment discussed in this specification can be implemented with respect to any composition (e.g., formulation) or method of the present disclosure. Furthermore, compositions (e.g., formulations) of the present disclosure can be used to achieve methods of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

Unless specified otherwise, the term "alkyl," when used alone or in combination with other groups or atoms, refers to a saturated linear or branched chain including 1 to about 10 hydrogen-substituted carbon atoms. Alkyl groups include, e.g., methyl, ethyl, propyl, isopropyl, n-butyl, 1-methylpropyl, isobutyl, t-butyl, 2,2-dimethylbutyl, n-pentyl, 2-methylpentyl, 3-methylpentyl, 4-methylpentyl, n-hexyl, n-heptyl, n-octyl, n-nonyl, n-decyl, and the like.

Unless specified otherwise, the term "alkenyl" refers to a partially unsaturated linear or branched chain including about 2 to about 10 hydrogen-substituted carbon atoms that contain at least one double bond. Alkenyl groups include, e.g., vinyl, allyl, 2-methylprop-1-enyl, but-1-enyl, but-2-enyl, but-3-enyl, buta-1,3-dienyl, penta-1,3-dienyl, penta-2,4-dienyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl, hepten-1-yl, octen-1-yl, nonen-1-yl, decen-1-yl, and the like.

Unless specified otherwise, the term "alkynyl" refers to a partially unsaturated linear or branched chain including about 2 to about 10 hydrogen-substituted carbon atoms that contains at least one triple bond. Alkynyl groups include, e.g., ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl, 1-heptynyl, 1-octynyl, 1-nonynyl, 1-decynyl, and the like.

Unless specified otherwise, the term "cycloalkyl" refers to a saturated or unsaturated ring including about 3 to about 10 carbon atoms, that may optionally be substituted with one or more identical or different substituents, e.g., one to three, one to six, one to eight, or one to ten substituents. Cycloalkyl groups include, e.g., cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl, cyclononyl, cyclodecyl, and the like.

Unless specified otherwise, the term "aryl" refers to an aromatic mono- or bicyclic group containing from about 5 to about 14 carbon atoms that may be optionally fused with a fully or partially saturated or unsaturated carbocyclic ring. Aryl groups include, e.g., phenyl, naphthyl, indanyl, and the like.

Unless specified otherwise, the term "alkanoyl" refers to a carbonyl (C=O) group bonded to an alkyl group. The term "alkenoyl" refers to a carbonyl (C=O) group bonded to an alkenyl group. The term "alkynoyl" refers to a carbonyl (C=O) group bonded to an alkynyl group. The term "cycloalkyl" refers to an alkane containing one or more rings of carbon atoms. A "cycloalkanoyl" refers to a carbonyl (C=O) group bonded to a cycloalkyl group. An "aryl carbonyl" refers to a carbonyl (C=O) bonded to an aryl group.

Unless specified otherwise, a "heterocycle" refers to a monocyclic non-aromatic hydrocarbon ring containing about 3 to about 10 carbon atoms, or a bicyclic non-aromatic hydrocarbon ring system containing about 7 to about 14 carbon atoms, wherein one or more of the carbon atoms of the in the hydrocarbon ring or ring system is replaced by a one heteroatom. Examples of heterocycles include but are not limited to azepan-1-yl, piperidinyl, e.g., piperidin-1-yl and piperidin-4-yl, piperazinyl, e.g., N-piperazinyl and 1-alkylpiperazine-4-yl, morpholine-4-yl, tetrahydrofuranyl, tetrahydrothienyl, pyrrolidinyl, tetrahydropyranyl, tetrahydrothiophen, sulfolanyl, sulfolenyl, oxazolinyl, isoxazolinyl, oxazolidinyl, oxazolidinon-yl. A "heterocycle carbonyl" refers to a carbonyl (C=O) bonded to a heterocycle group.

Unless specified otherwise, a "heteroaryl" refers to an aromatic compound containing at least one heteroatom. Examples of heteroaryl groups include but are not limited to pyrrolyl, dihydropyrrolyl, pyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, quinolizinyl, pyrazinyl, pyridazinyl, pyrimidinyl, pyranyl, tetrahydropyranyl, 1,2,3-triazinyl, 1,2,4-triazinyl, 1,3,5-triazinyl, chromenyl, morpholinyl, diazepinyl, benzodiazepinyl, and the like. A "heteroaryl carbonyl" refers to a carbonyl (C=O) bonded to a heteroaryl group.

In some embodiments, any of the carbon chain substituents described herein, e.g., alkyl, alkanoyl, alkenoyl, alkynoyl, alkanoyl, etc., can have one or more of the carbons in the carbon chain replaced by one or more heteroatoms, i.e., an atom other than a carbon or hydrogen, e.g., nitrogen, oxygen, sulfur, phosphorus. In some embodiments, the substituents described herein, e.g., alkyl group, alkenyl group, alkynyl group, cycloalkyl group, aryl group, heterocycle, heteroaryl, alkanoyl group, alkenoyl group, alkynoyl group, cycloalkanoyl group, aryl carbonyl group, heterocyle carbonyl group, heteroaryl carbonyl group, etc., can be "substituted or unsubstituted." The term "substituted" refers to the substitution of a hydrogen on the substituent with a different group, e.g., a hydroxyl, halide, alkyl (e.g., $C_{1-6}$ alkyl), alcohol, ketone, and the like. The term "unsubstituted" refers where the substituent has not had a hydrogen substituted with a different group.

A "linear" molecule contains a single backbone. For example, a "linear $C_1$-$C_n$" molecule includes one to n number of carbon atoms, wherein each carbon atom is bound to its two neighbors and to two hydrogen atoms (with the exception of the terminal carbons, which are bound to only one carbon atom and three hydrogen atoms). A "branched" molecule contains a nonlinear backbone, wherein branches can sprout from one or more atoms of the main backbone. For example, a "branched $C_1$-$C_n$" molecule is derived from a linear $C_1$-$C_n$ molecule, except that at least one of the hydrogen atoms bound to at least one of the carbons is replaced with a substituent, e.g., an alkyl group.

Any of the cyclic groups described herein (e.g., cycloalkyl, aryl, heterocycle, heteroaryl) can be substituted or unsubstituted. For example, a substituted cycloalkane can have substituents at any of the atoms forming the ring. Substituents can include any of the groups described herein, e.g., alkyl, alkenyl, alkynyl, etc.

In some embodiments, the present disclosure provides a process for the preparation of a compound of Formula (I) [Trifarotene], or a salt thereof

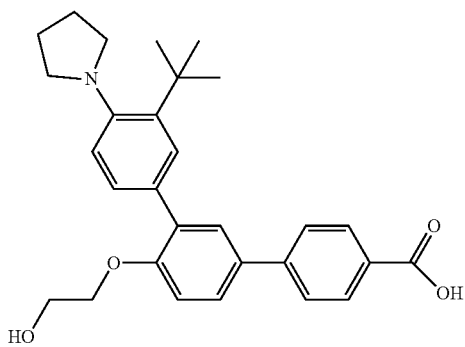

(I)

comprising hydrolyzing a compound of Formula (V)

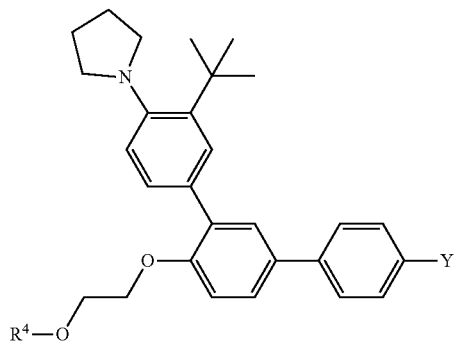

(V)

wherein $R^4$ is hydrogen, a substituted or unsubstituted linear or branched $C_1$-$C_8$ alkanoyl group, a substituted or unsubstituted linear or branched $C_1$-$C_8$ alkenoyl group, a substituted or unsubstituted linear or branched $C_1$-$C_8$ alkynoyl group, a substituted or unsubstituted cycloalkanoyl group, a substituted or unsubstituted aryl carbonyl group, a substituted or unsubstituted heterocyle carbonyl group, a substituted or unsubstituted heteroaryl carbonyl group, or a $C_1$-$C_8$ alkanoyl group comprising a heteroatom; and wherein Y is a nitrile (CN) or amide ($CONH_2$); to obtain the compound of Formula (I).

In some embodiments, the compound of Formula (I) is Trifarotene. In some embodiments, the compound of Formula (I) is Trifarotene-HCl. In some embodiments, the compound of Formula (I) is a Trifarotene Na salt.

In some embodiments, $R^4$ is hydrogen. In embodiments, $R^4$ is an alkanoyl group. In some embodiments, $R^4$ is a formyl group (—COH). In embodiments, $R^4$ is an acetyl group (—$COCH_3$). In some embodiments, the compound of Formula (V) is selected from the following:

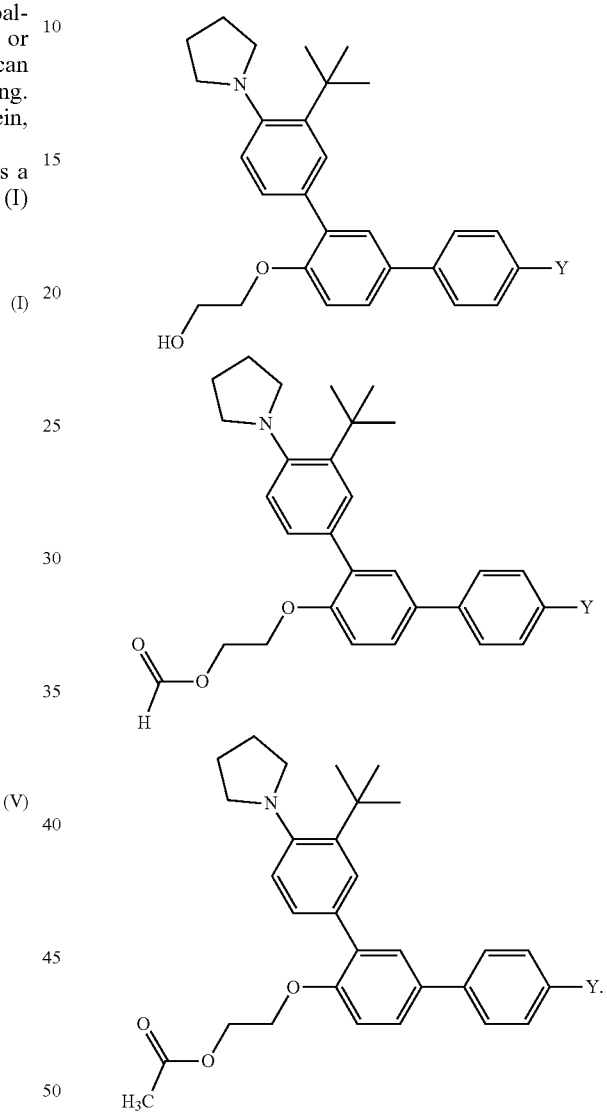

In some embodiments, Y is a nitrile. In some embodiments, Y is an amide. In some embodiments, $R^4$ is hydrogen, and Y is a nitrile or amide. In some embodiments, $R^4$ is an alkanoyl, and Y is a nitrile or amide. In some embodiments, $R^4$ is formyl, and Y is a nitrile or amide. In some embodiments, $R^4$ is acetyl, and Y is a nitrile or amide.

In some embodiments, $R^4$ is an alkenoyl, and Y is a nitrile or amide. In some embodiments, $R^4$ is an alkynoyl, and Y is a nitrile or amide. In some embodiments, $R^4$ is a substituted cycloalkanoyl, and Y is a nitrile or amide. In some embodiments, $R^4$ is an unsubstituted cycloalkanoyl, and Y is a nitrile or amide. In some embodiments, $R^4$ is a substituted aryl carbonyl group, and Y is a nitrile or amide. In some embodiments, $R^4$ is an unsubstituted aryl carbonyl group, and Y is a nitrile or amide. In some embodiments, $R^4$ is a substituted heterocyle carbonyl group, and Y is a nitrile or amide. In some embodiments, R⁴ is an unsubstituted heterocyle carbonyl group, and Y is a nitrile or amide. In some embodiments, R⁴ is a substituted heteroaryl carbonyl group, and Y is a nitrile or amide. In some embodiments, R⁴ is an unsubstituted heteroaryl carbonyl group, and Y is a nitrile or amide. In some embodiments, R⁴ is a $C_1$-$C_8$ alkanoyl group comprising a heteroatom, and Y is a nitrile or amide.

In some embodiments, the compound of Formula (V) is selected from the following:

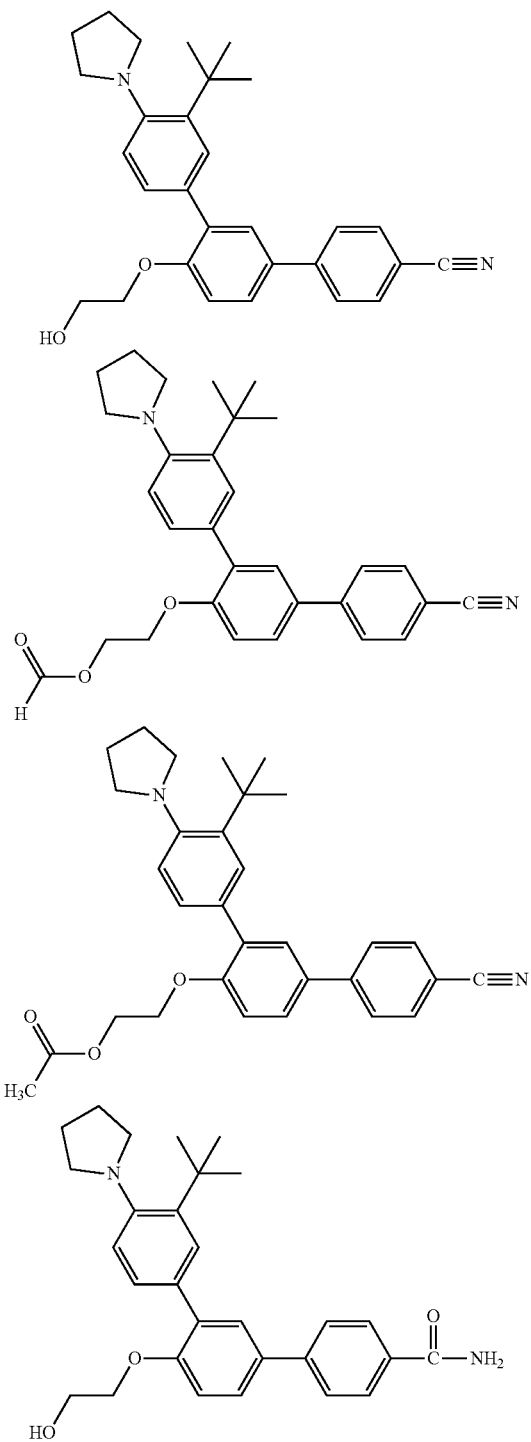

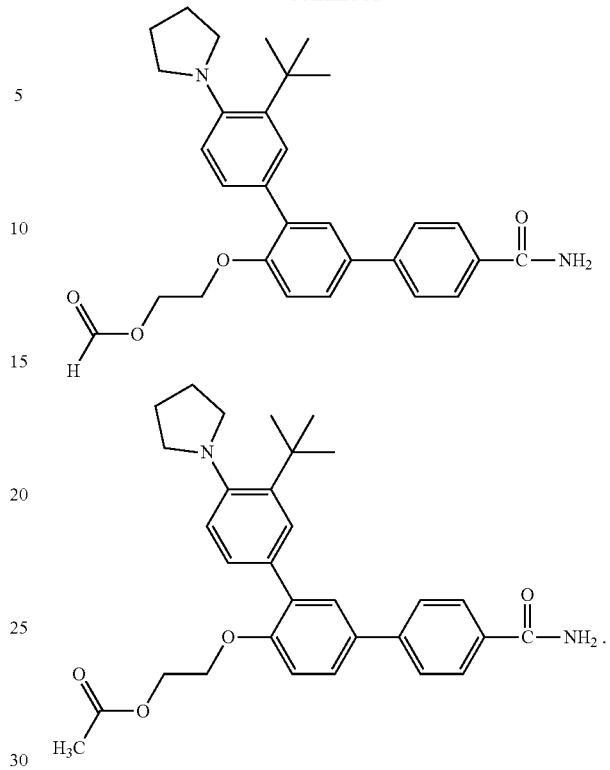

The term "hydrolysis" or variants thereof such as "hydrolyze" or "hydrolyzing," refers to a reaction in which water is a reactant and becomes part of the reaction product, typically as a hydroxyl (—OH) group. Hydrolysis of nitriles or amides can form a carboxylic acid (—COOH). In some embodiments, hydrolysis is performed in the presence of water and a co-solvent. Examples of co-solvents that can be used with water for hydrolysis reactions include but are not limited to alcohols, e.g., methanol, ethanol, propanol, isopropanol, n-butanol, tert-butanol, sec-butanol, and isobutyl alcohol; methylene chloride; acetonitrile; ethyl acetate; and tetrahydrofuran (THF). In some embodiments, the hydrolysis is performed in the presence of water and an alcohol. In some embodiments, the alcohol is methanol (MeOH), ethanol (EtOH), propanol (PrOH), isopropanol (IPA), or any mixture thereof. In some embodiments, the hydrolysis is performed in the presence of water and ethanol.

In some embodiments, hydrolysis is performed further in the presence of an acid or a base. In some embodiments, the acid comprises hydrochloric acid (HCl), sulfuric acid ($H_2SO_4$), nitric acid ($HNO_3$), hydrobromic acid (HBr), hydroiodic acid (HI), perchloric acid ($HClO_4$), chloric acid ($HClO_3$), sulfurous acid ($H_2SO_3$), methanoic acid ($HCO_2H$), phosphoric acid ($H_3PO_4$), nitrous acid ($HNO_2$), hydrofluoric acid (HF), or any mixture thereof. In some embodiments, the base comprises sodium hydroxide (NaOH), potassium hydroxide (KOH), lithium hydroxide (LiOH), barium hydroxide ($Ba(OH)_2$), or any mixture thereof.

In some embodiments, R⁴ is hydrogen, and Y is hydrolyzed. In some embodiments, Y is hydrolyzed to form a carboxylic acid. In some embodiments, R⁴ comprises a carbonyl as described herein, and the carbonyl together with the oxygen attached thereto are hydrolyzed to generate a hydroxyl group. In some embodiments, R⁴ and Y are capable of being hydrolyzed under the same reaction conditions. In some embodiments, R⁴ and Y are hydrolyzed simultaneously.

In some embodiments, the compound of Formula (V) is present in the hydrolysis reaction at about 0.1 to about 1 mol/L (solvent), about 0.2 to about 0.8 mol/L (solvent), or about 0.3 to about 0.5 mol/L (solvent). In some embodiments, the compound of Formula (V) is present in the hydrolysis reaction at about 0.1, about 0.2, about 0.3, about 0.4, about 0.5, about 0.6, about 0.7, about 0.8, about 0.9, or about 1 mol/L (solvent). In some embodiments, the hydrolysis of the compound of Formula (V) is performed in an acidic condition. In some embodiments, the hydrolysis is performed at a pH of about 4 to about 6.5, about 4.2 to about 6.2 about 4.5 to about 6, about 4.7 to about 5.7, or about 5 to about 5.5. In some embodiments, the hydrolysis reaction is performed at pH about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, or about 6.5.

In some embodiments, the disclosure provides a process for preparing the compound of Formula (V) wherein $R^4$ is hydrogen. In some embodiments, the compound of Formula (V) is prepared by hydrolyzing a compound of Formula (IV)

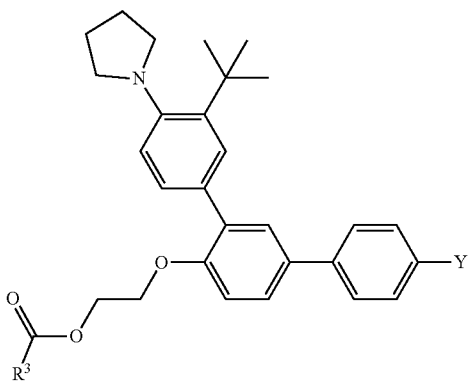

(IV)

in the presence of a base, wherein $R^3$ is hydrogen, a hydroxyl group, a substituted or unsubstituted linear or branched $C_1$-$C_8$ alkyl group, a substituted or unsubstituted linear or branched $C_1$-$C_8$ alkenyl group, a substituted or unsubstituted linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; and wherein Y is a nitrile (CN) or amide ($CONH_2$); to obtain the compound of Formula (V). In some embodiments, the ester (—$COOR^3$) of the compound of Formula (IV) is hydrolyzed to form a hydroxyl group (—OH). In some embodiments, $R^4$ of the compound of Formula (V) is hydrogen.

Y in the compound of Formula (IV) is as defined herein for the compound of Formula (V). In some embodiments, $R^3$ is hydrogen, and Y is a nitrile or amide. In some embodiments, $R^3$ is methyl, and Y is a nitrile or amide. In some embodiments, $R^3$ is hydroxyl, and Y is a nitrile or amide. In some embodiments, $R^3$ is methyl, and Y is a nitrile.

In some embodiments, the hydrolysis of the compound of Formula (IV) is performed in the presence of water and a co-solvent. Exemplary co-solvents are provided herein. In some embodiments, the hydrolysis of the compound of Formula (IV) is performed in a solvent comprising water, methanol (MeOH), ethanol (EtOH), propanol (PrOH), iso-propanol (IPA), or any mixture thereof. In some embodiments, the solvent comprises water and ethanol.

In some embodiments, the hydrolysis of the compound of Formula (IV) is performed in the presence of a base. Exemplary bases for hydrolysis reactions are provided herein. In some embodiments, the base for the hydrolysis of the compound of Formula (IV) comprises sodium hydroxide (NaOH), potassium hydroxide (KOH), lithium hydroxide (LiOH), barium hydroxide ($Ba(OH)_2$), or any mixture thereof.

In some embodiments, the compound of Formula (IV) is present in the hydrolysis reaction at about 0.01 to about 0.5 mol/L (solvent), about 0.02 to about 0.2 mol/L (solvent), about 0.03 to about 0.1 mol/L (solvent), about 0.04 to about 0.08 mol/L (solvent), or about 0.05 to about 0.07 mol/L (solvent). In some embodiments, the compound of Formula (IV) is present in the hydrolysis reaction at about 0.01, about 0.02, about 0.03, about 0.04, about 0.05, about 0.06, about 0.07, about 0.08, about 0.09, or about 0.1 mol/L (solvent). In some embodiments, the base is added to the hydrolysis reaction at about 1, about 2, about 3, about 4, about 5, about 6, about 7, about 8, about 9, or about 10 molar equivalents relative to the compound of Formula (IV). In some embodiments, the base is added to the hydrolysis reaction at about 0.1 to about 1 mol/L (solvent), about 0.2 to about 0.8 mol/L (solvent), about 0.3 to about 0.6 mol/L (solvent), or about 0.4 to about 0.5 mol/L (solvent).

In some embodiments, the disclosure further provides a process for preparing the compound of Formula (IV), comprising reacting a compound of Formula (II)

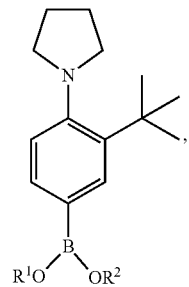

(Formula II)

with a compound of Formula (III)

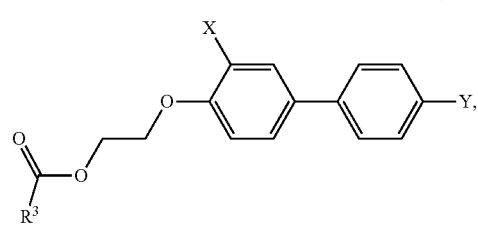

(Formula III)

wherein $R^1$ and $R^2$ are independently hydrogen, a linear or branched $C_1$-$C_3$ alkyl, or a pinacolate, and wherein $R^1$ and $R^2$ can be the same or different, or $R^1$ and $R^2$ together form a pinacolate, with a compound of Formula (III)

in the presence of a catalyst, wherein $R^3$ is hydrogen, a hydroxyl group, a linear or branched $C_1$-$C_8$ alkyl, a linear or branched $C_1$-$C_8$ alkenyl group, a linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; wherein X is a halogen or triflate; and wherein Y is a nitrile or amide, to obtain the compound of Formula (IV).

In some embodiments, $R^1$ and $R^2$ of the compound of Formula (II) are independently hydrogen. In some embodiments, $R^1$ and $R^2$ of the compound of Formula (II) are independently a linear or branched $C_1$-$C_3$ alkyl group. In some embodiments, $R^1$ and $R^2$ of the compound of Formula (II) together form a pinacolate.

In some embodiments, the compound of Formula (II) is selected from the following:

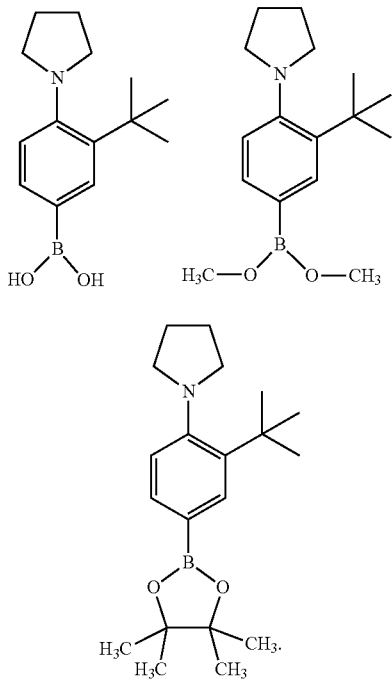

$R^3$ and Y of the compound of Formula (III) are defined as above for the compound of Formula (IV). In some embodiments, X of the compound of Formula (III) is a leaving group for a Suzuki coupling reaction. Examples of leaving groups for Suzuki reactions are further provided in, e.g., Liu et al., *Org Lett* 7(6):1149-1151 (2005); El-Berjawi et al., *Dyes Pigments* 159:551-556 (2018); Chemler et al., *Angew Chem Int Ed* 40:4544 (2001). In some embodiments, X is a halogen, e.g., fluorine, chlorine, bromine, or iodine. In some embodiments, X is a triflate (—$OSO_2CF_3$; also abbreviated as —OTf) group. In some embodiments, $R^3$ is hydrogen, Y is a nitrile or amide, and X is a halogen or triflate. In some embodiments, $R^3$ is methyl, Y is a nitrile or amide, and X is a halogen or triflate. In some embodiments, $R^3$ is a hydroxyl, Y is a nitrile or amide, and X is a halogen or triflate. In some embodiments, $R^3$ is methyl, Y is a nitrile, and X is iodine.

In some embodiments, the compound of Formula (III) is selected from the following:

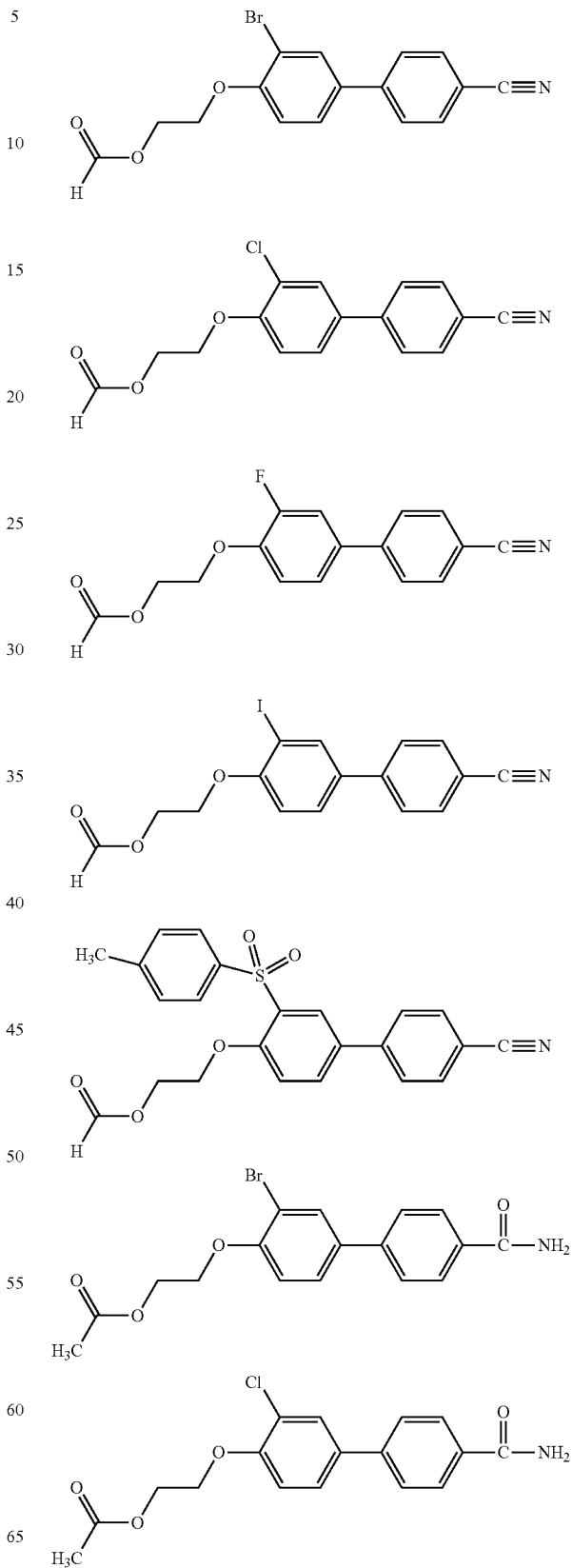

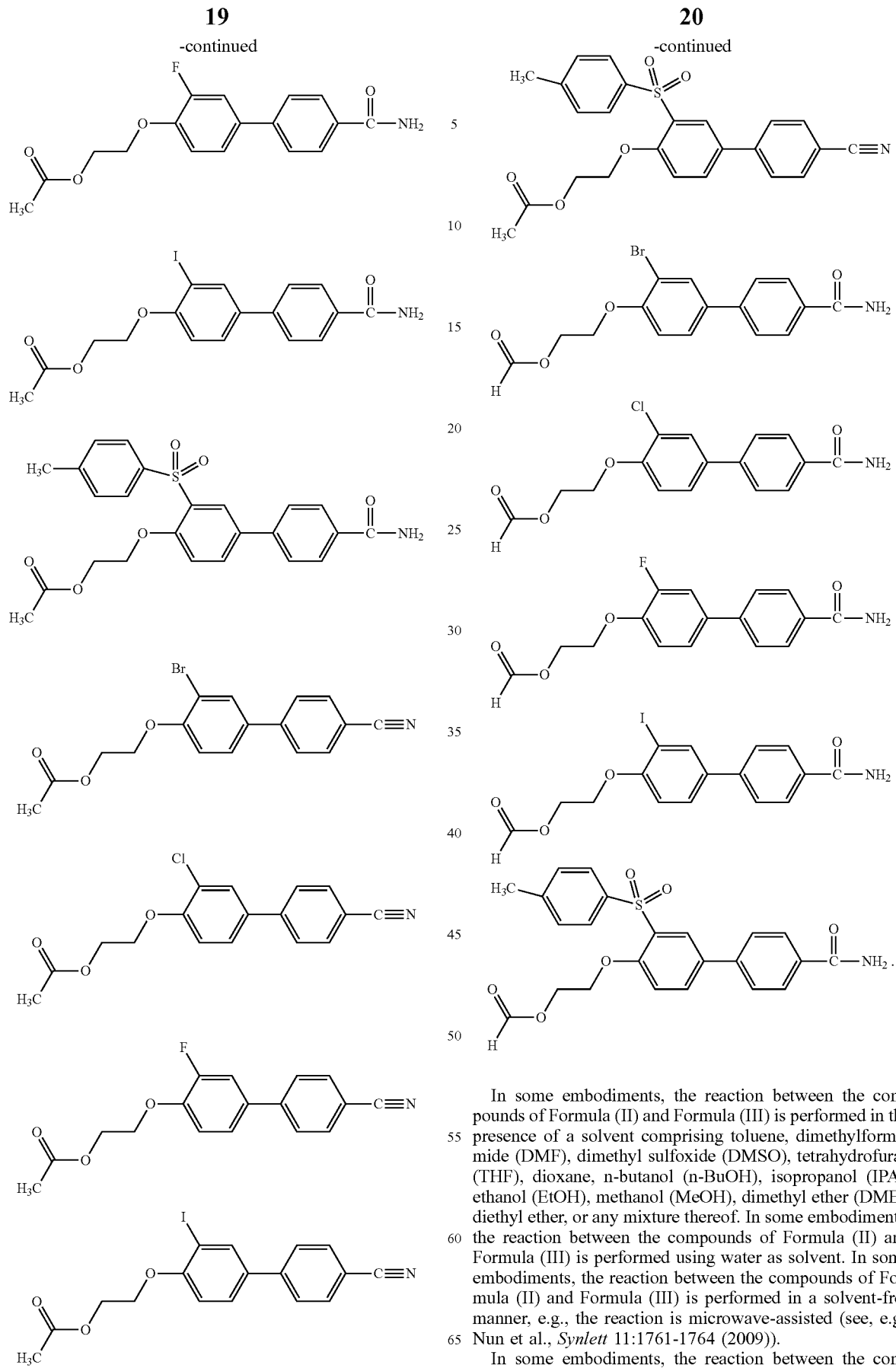

In some embodiments, the reaction between the compounds of Formula (II) and Formula (III) is performed in the presence of a solvent comprising toluene, dimethylformamide (DMF), dimethyl sulfoxide (DMSO), tetrahydrofuran (THF), dioxane, n-butanol (n-BuOH), isopropanol (IPA), ethanol (EtOH), methanol (MeOH), dimethyl ether (DME), diethyl ether, or any mixture thereof. In some embodiments, the reaction between the compounds of Formula (II) and Formula (III) is performed using water as solvent. In some embodiments, the reaction between the compounds of Formula (II) and Formula (III) is performed in a solvent-free manner, e.g., the reaction is microwave-assisted (see, e.g., Nun et al., *Synlett* 11:1761-1764 (2009)).

In some embodiments, the reaction between the compounds of Formula (II) and Formula (III) is performed in the presence of a base comprising potassium carbonate ($K_2CO_3$), potassium acetate ($CH_3CO_2K$), potassium phosphate ($K_3PO_4$), potassium tert-butoxide (KOtBu), sodium carbonate ($Na_2CO_3$), sodium bicarbonate ($NaHCO_3$), sodium methoxide (NaOMe), sodium tert-butoxide (NaOtBu) cesium carbonate ($Cs_2CO_3$), silver phosphate ($Ag_3PO_4$), silver oxide ($Ag_2O$), thallium carbonate ($Tl_2CO_3$), thallium ethoxide (TlOEt), tert-butylamine (t-BuNH$_2$), potassium hydroxide (KOH), sodium hydroxide (NaOH), lithium hydroxide (LiOH), barium hydroxide (Ba(OH)$_2$), thallium hydroxide (TlOH), or combination thereof.

In some embodiments, the catalyst for the reaction between the compounds of Formula (II) and Formula (III) comprises a metal selected from palladium (Pd), copper (Cu), nickel (Ni), iron (Fe), zinc (Zn), or rhodium (Rh). In some embodiments, the catalyst comprises a metal selected from Pd, Cu, or Ni. In some embodiments, the catalyst comprises 1 to 6 atoms of the metal. In some embodiments, the catalyst comprises 2 to 5 atoms of the metal. In some embodiments, the catalyst comprises 2 to 4 atoms of the metal. In some embodiments, the catalyst comprises 1, 2, 3, 4, 5, or 6 atoms of the metal. Palladium-catalyzed coupling reactions are further described, e.g., in US 2006/0264629 and US 2010/0184739.

In some embodiments, the catalyst is a palladium catalyst. In some embodiments, the palladium catalyst is Pd(PPh$_3$)$_2$Cl$_2$ [bis(triphenylphosphine)palladium(II) dichloride]; Pd(PPh$_3$)$_4$ [tetrakis(triphenylphosphine)palladium(0)]; Pd(OAc)$_2$ [palladium(II) diacetate]; XPhos Pd-G3 [(2-dicyclohexylphosphino-2',4',6'-triisopropyl-1,1'-biphenyl)[2-(2'-amino-1,1'-biphenyl)]palladium(II) methanesulfonate]; SPhos-Pd-G2 [chloro(2-dicyclohexylphosphino-2',6'-dimethoxy-1,1'-biphenyl)[2-(2'-amino-1,1'-biphenyl)]palladium (II)]; CATACXIUM® A Pd G3 (mesylate[(di(1-adamantyl)-n-butylphosphine)-2-(2'-amino-1,1'-biphenyl)]palladium(II) or [(di(1-adamantyl)-butylphosphine)-2-(2'-amino-1,1'-biphenyl)]palladium(II) methanesulfonate); APhos Pd G3 (palladium G3-(4-(N,N-dimethylamino)phenyl)di-tert-butylphosphine] or [4-(di-tert-butylphosphino)-N,N-dimethylaniline-2-(2'-aminobiphenyl)]palladium(II) methanesulfonate); P(Cy$_3$) Pd-G3 (palladium G3-tricyclohexylphosphine or [(tricyclohexylphosphine)-2-(2'-aminobiphenyl)]palladium(II) methanesulfonate); Allylpalladium (II) chloride dimer (bis(allyl)dichlorodipalladium); or Pd(dppf)Cl$_2$ [1,1'-Bis(diphenylphosphino)ferrocene]dichloropalladium(II)].

In some embodiments, the catalyst is a copper catalyst. In some embodiments, the copper catalyst is copper(I) chloride, [(o-(di-tert-butylphosphino)-N,N-dimethylaniline)copper iodide]$_2$, [(o-(di-tert-butylphosphino)-N,N-dimethylaniline)copper fluoride]$_2$. In some embodiments, the catalyst is a nickel catalyst. In some embodiments, the nickel catalyst is NiCl$_2$, NiBr$_2$, NiI$_2$, G$_3$DenP-Ni, (dppf)Ni(cinnamyl)Cl, (PCy$_3$)$_2$NiCl$_2$, or Ni(cod)$_2$. Further exemplary catalysts are provided in, e.g., Tasker et al., *Nature* 509(7500):299-309 (2014); Yang et al., *Angew Chem Int Ed Engl* 50(17):3904-3907 (2011); Barder et al., *J Am Chem Soc* 127(13):4685-4696 (2005); Bedford et al., *Chem Commun (Camb)* 42:6430-6432 (2009); and *Catalysts* vol. 9, ISSN 2073-4344 (2019).

In some embodiments, the reaction between the compounds of Formula (II) and Formula (III) is performed further in the presence of a ligand. In some embodiments, the ligand is a phosphine ligand, a carbon ligand, or a nitrogen ligand. In some embodiments, the ligand is PPh$_3$, PCy$_3$, P(o-tolyl)$_3$, P(i-Pr)$_3$, P(O-Pr-i)$_3$, n-BuP(1-Ad)$_2$, P(t-Bu)$_2$(p-NMe$_2$-Ph), a dialkylbiaryl ligand (e.g., as described in Martin et al., *Acc Chem Res* 41:1461 (2008)), a bidentate phosphine ligand such as DPPF, DPPE or DPPP, a carbene-type ligand (e.g., as described in Kuwano et al., *Org Lett* 7:945 (2005)), an olefin-type ligand (e.g., as described in Tao et al., *J Org Chem* 69:4330 (2004)), an amine, or imine (e.g., as described in Tao et al., *J Org Chem* 69:4330 (2004)). In some embodiments, the ligand and catalyst are provided in the reaction as a preformed complex. For example, Pd(PPh$_3$)$_4$ includes both a palladium catalyst and phosphine ligand. In some embodiments, the process for preparing a compound of Formula (IV) comprises preparing a catalyst comprising a metal and a ligand.

In some embodiments, the reaction does not include a catalyst. In some embodiments, the reaction does not include a ligand. Further exemplary reaction conditions are discussed in, e.g., Suzuki, *J Organometallic Chem* 576:147-168 (1999); Miyaura et al., *Chem Rev* 95:2457-2483 (1995); Chemler et al., *Angew Chem Int Ed Engl* 40:4544-4568 (2001); Franzén, *Can J Chem* 78:957-962 (2000); Suzuki, *Proc Jpn Acad, Ser B.* 80(8):359 (2004); and Paul et al., *RSC Adv* 5:42193 (2015).

In some embodiments, the compounds of Formula (II) and Formula (III) are added to the reaction at a molar ratio of about 1:10, about 1:5, about 1:4, about 1:3, about 1:2, about 1:1, about 1:0.75, about 1:0.5, about 1:0.25, about 1:0.1, or about 1:0.05. In some embodiments, the compounds of Formula (II) and (III) are added an amount of about 0.01 to about 1 mol/L (solvent), about 0.05 to about 0.5 mol/L (solvent), about 0.1 to about 0.4 mol/L (solvent), about 0.15 to about 0.35 mol/L (solvent), or about 0.2 to about 0.3 mol/L (solvent).

In some embodiments, the catalyst is added to the reaction at about 0.001 to about 1, about 0.002 to about 0.5, about 0.003 to about 0.1, about 0.004 to about 0.075, about 0.005 to about 0.05, about 0.006 to about 0.025, about 0.007 to about 0.01, or about 0.008 to about 0.009 molar equivalents relative to the compounds of Formula (II) or Formula (III). In some embodiments, the catalyst is added to the reaction at about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, about 0.2, about 0.3, about 0.5, about 0.6, about 0.7, about 0.8, about 0.9, or about 1 molar equivalents relative to the compounds of Formula (II) or Formula (III).

In some embodiments, the base is added to the reaction at a about 0.1 to about 10, about 0.5 to about 8, about 1 to about 6, or about 2 to about 4 molar equivalents relative to the compounds of Formula (II) or Formula (III). In some embodiments, the base is added to the reaction at about 0.1, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 molar equivalents relative to the compounds of Formula (II) or Formula (III).

In some embodiments, the disclosure provides a process for the preparation of a compound of formula (I) [Trifarotene], or a salt thereof

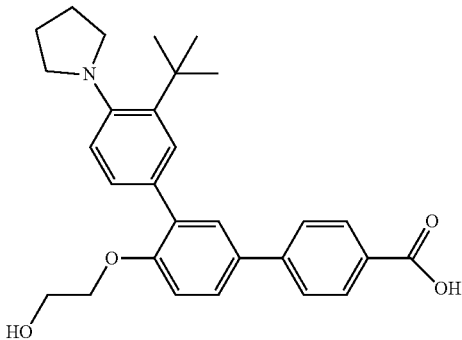
(I)

comprising reacting a compound of formula (II)

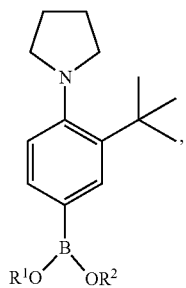
(II)

wherein $R^1$ and $R^2$ are independently hydrogen or a linear or branched $C_1$-$C_3$ alkyl, wherein $R^1$ and $R^2$ can be the same or different; or $R^1$ and $R^2$ together form a pinacolate, with a compound of formula (III)

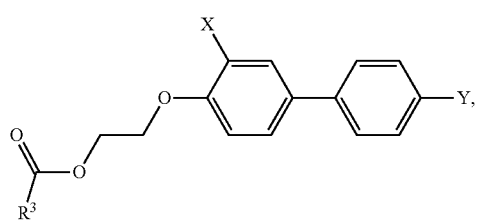
(III)

wherein $R^3$ is a substituted or unsubstituted linear or branched $C_1$-$C_8$ alkyl, a substituted or unsubstituted linear or branched $C_1$-$C_8$ alkenyl group, a substituted or unsubstituted linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; wherein X is a halogen or triflate; and wherein Y is a nitrile (CN) or amide (CONH$_2$), in the presence of a catalyst, to obtain a compound of formula (IV)

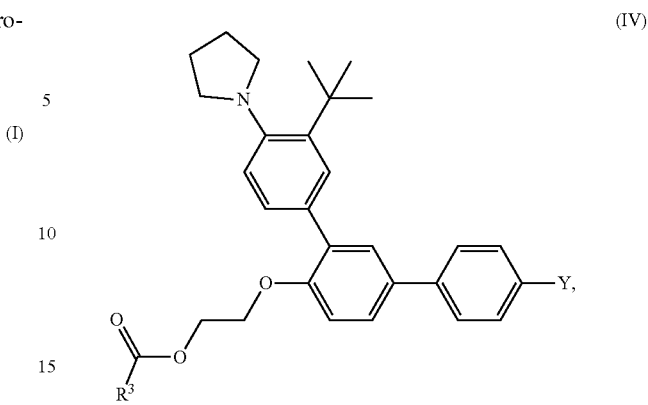
(IV)

wherein $R^3$ is as defined above; and hydrolyzing the compound of formula (IV) in the presence of a base, to obtain Trifarotene. $R^1$, $R^2$, $R^3$, $R^4$, X, and Y, and the various reactions and conditions are further described herein. In some embodiments, $R^3$ is methyl, X is iodine, and Y is nitrile.

Figure 9:
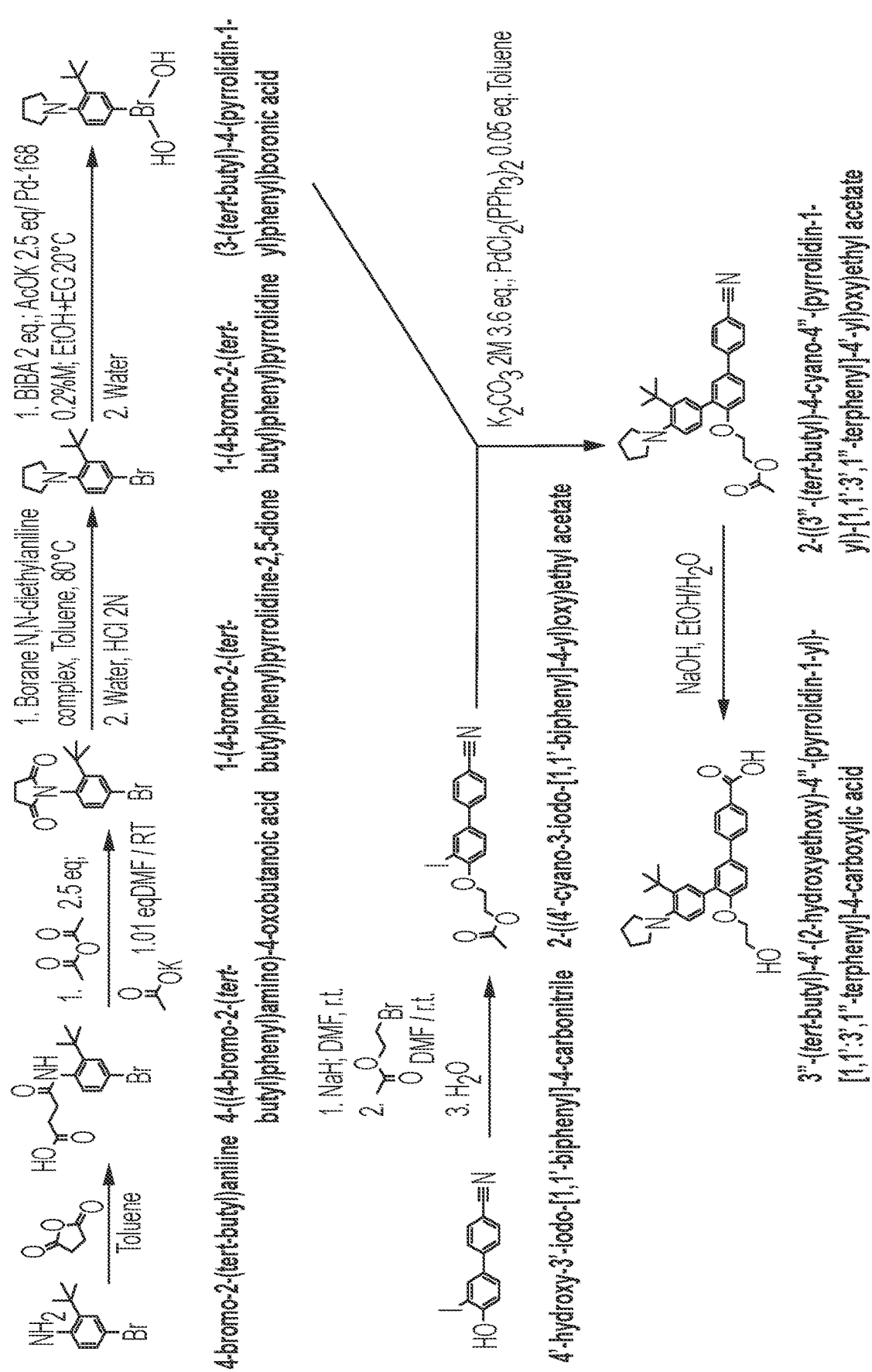
FIG. 9 is an exemplary process for the preparation of Trifarotene [Formula (I)] as described in embodiments herein.

An exemplary process for the preparation of Trifarotene [Formula (I)] as described in embodiments herein is shown in FIG. 9.

In some embodiments, the disclosure provides a process for preparing a compound of Formula (II)

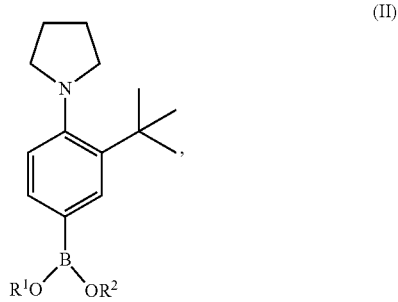
(II)

wherein $R^1$ and $R^2$ are independently hydrogen or a linear or branched $C_1$-$C_3$ alkyl, wherein $R^1$ and $R^2$ can be the same or different; or $R^1$ and $R^2$ together form a pinacolate, comprising reacting

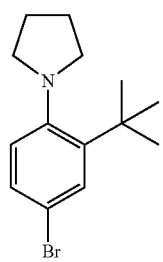 [SMILES: CC(C)(C)c1cc(Br)ccc1N1CCCC1]

with a compound comprising —$R^1$OBOR$^2$— in the presence of a salt and a catalyst, wherein $R^1$ and $R^2$ are defined as above for the compound of Formula (II). In some embodiments, the catalyst is a palladium catalyst. In some embodiments, the catalyst comprises P(tBu)$_3$. In some embodiments, the catalyst is Pd-162 ([P(tBu)$_3$] Pd(crotyl)Cl), Pd-168 ([P(tBu)₃] Palladacycle), or Pd-216 ({Pd(μ-I) [P(t-Bu)₃]}₂). In some embodiments, the reaction is performed at about 15° C. to about 35° C., about 18° C. to about 32° C., about 20° C. to about 30° C., about 22° C. to about 28° C., or about 24° C. to about 26° C. In some embodiments, the process for preparing the compound of Formula (II) provided herein is performed at room temperature. When compared with previously described methods, e.g., as described in WO 2006/066978, which perform the reaction under harsh conditions (e.g., at −78° C.), the present process greatly reduces the complexity and shortens preparation time.

In some embodiments, the present disclosure provides novel compounds. In some embodiments, the novel compounds described herein are used in the preparation of Trifarotene. The novel compounds provided herein can advantageously simplify the Trifarotene preparation process.

In some embodiments, the disclosure provides a compound of Formula (III)

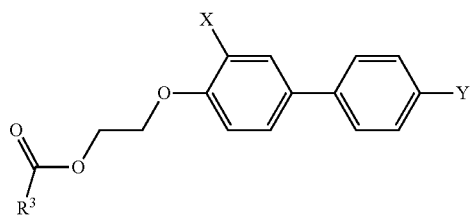

(III)

wherein $R^3$ is a substituted or unsubstituted linear or branched $C_1$-$C_8$ alkyl group, substituted or unsubstituted linear or branched $C_1$-$C_8$ alkenyl group, substituted or unsubstituted linear or branched $C_1$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group comprising a heteroatom; wherein X is a halogen or triflate; and wherein Y is a nitrile or amide. $R^3$, X, and Y are further described herein.

In some embodiments, the compound of Formula (III) is selected from the following:

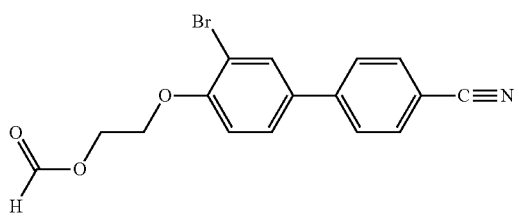

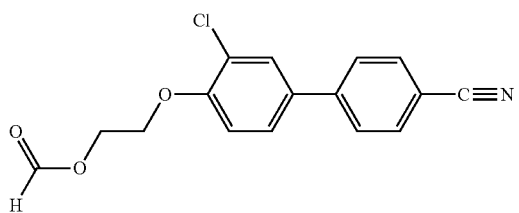

-continued

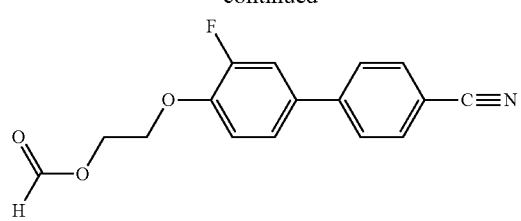

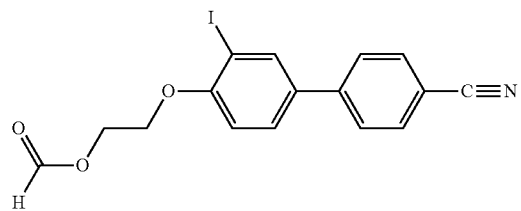

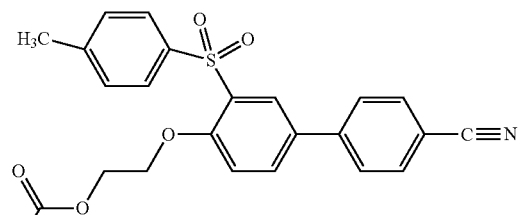

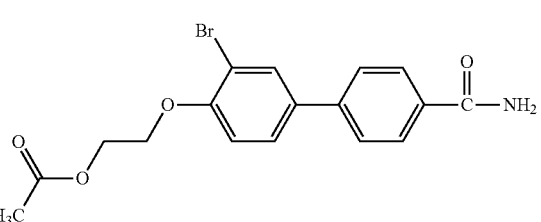

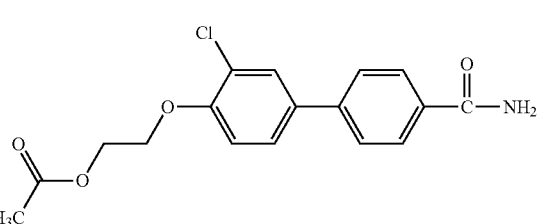

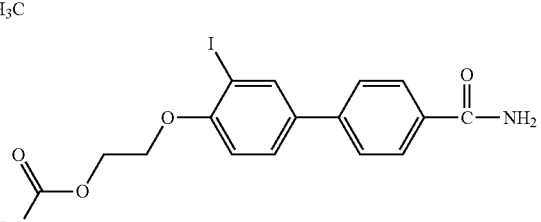

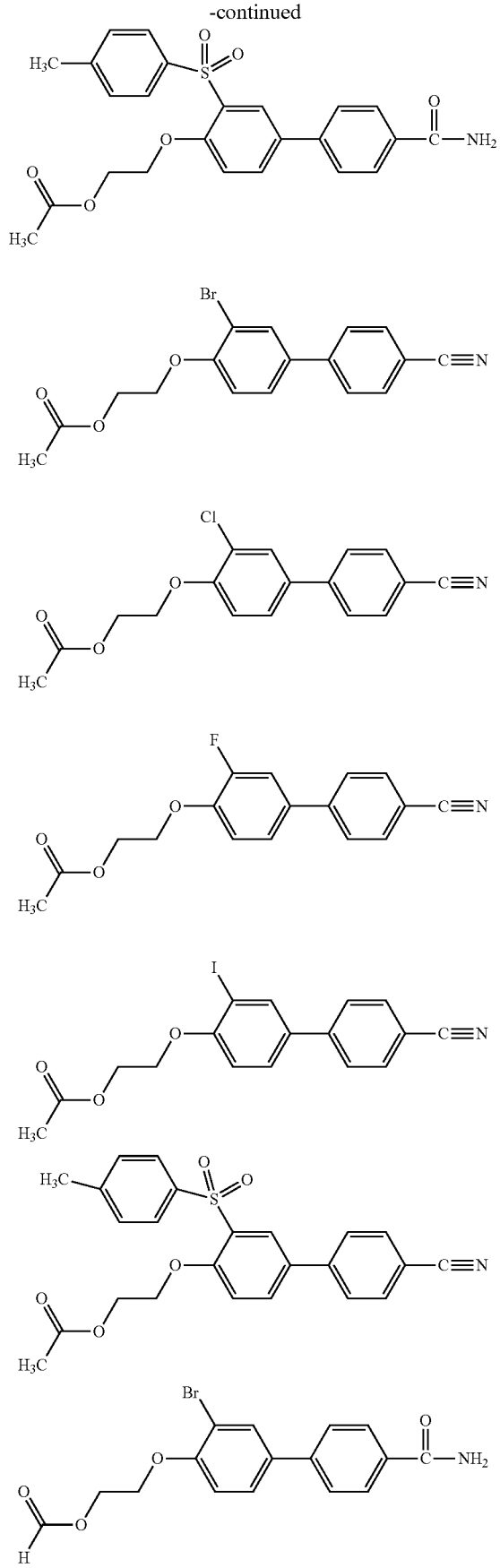
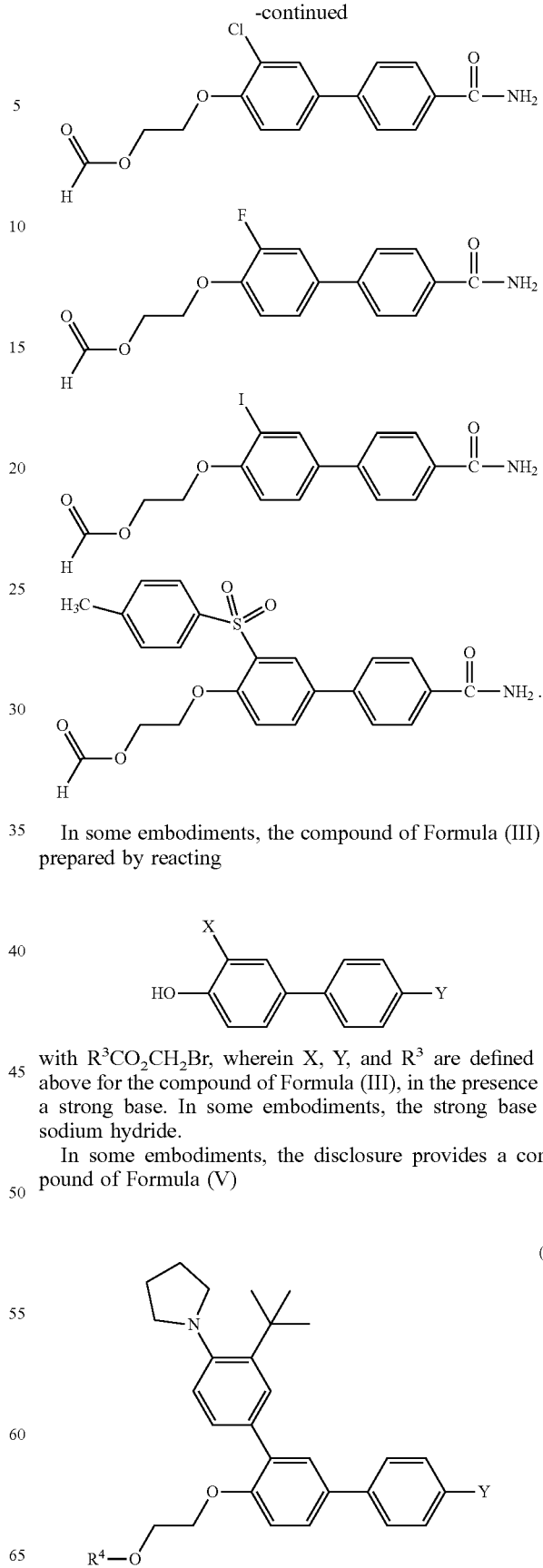
In some embodiments, the compound of Formula (III) is prepared by reacting
with $R^3CO_2CH_2Br$, wherein X, Y, and $R^3$ are defined as above for the compound of Formula (III), in the presence of a strong base. In some embodiments, the strong base is sodium hydride.
In some embodiments, the disclosure provides a compound of Formula (V)
(V)

wherein R⁴ is hydrogen, a substituted or unsubstituted linear or branched $C_1$-$C_8$ alkanoyl group, a substituted or unsubstituted linear or branched $C_1$-$C_8$ alkenoyl group, a substituted or unsubstituted linear or branched $C_1$-$C_8$ alkynoyl group, a substituted or unsubstituted cycloalkanoyl group, a substituted or unsubstituted aryl carbonyl group, a substitute or unsubstituted heterocyle carbonyl group, a substituted or unsubstituted heteroaryl carbonyl group, or a $C_1$-$C_8$ alkanoyl group comprising a heteroatom; and wherein Y is a nitrile (CN) or amide (CONH₂).

R⁴ and Y are further described herein. In some embodiments, R⁴ is hydrogen. In some embodiments, R⁴ is a substituted or unsubstituted linear or branched $C_1$-$C_8$ alkanoyl group, a substituted or unsubstituted linear or branched $C_1$-$C_8$ alkenoyl group, a substituted or unsubstituted linear or branched $C_1$-$C_8$ alkynoyl group, a substituted or unsubstituted cycloalkanoyl group, a substituted or unsubstituted aryl carbonyl group, a substitute or unsubstituted heterocyle carbonyl group, a substituted or unsubstituted heteroaryl carbonyl group, or a $C_1$-$C_8$ alkanoyl group comprising a heteroatom.

In some embodiments, R⁴ is a unsubstituted linear or branched $C_1$-$C_8$ alkanoyl group, a unsubstituted linear or branched $C_1$-$C_8$ alkenoyl group, a unsubstituted linear or branched $C_1$-$C_8$ alkynoyl group, a unsubstituted cycloalkanoyl group, a unsubstituted aryl carbonyl group, a unsubstituted heterocyle carbonyl group, a unsubstituted heteroaryl carbonyl group, or a $C_1$-$C_8$ alkanoyl group comprising a heteroatom.

In some embodiments, R⁴ is a unsubstituted linear or branched $C_1$-$C_4$ alkanoyl group, a unsubstituted linear or branched $C_1$-$C_4$ alkenoyl group, a unsubstituted linear or branched $C_1$-$C_4$ alkynoyl group, or a $C_1$-$C_4$ alkanoyl group comprising a heteroatom.

In some embodiments, R⁴ is acetyl.

In some embodiments, the compound of Formula (V) is selected from the following:

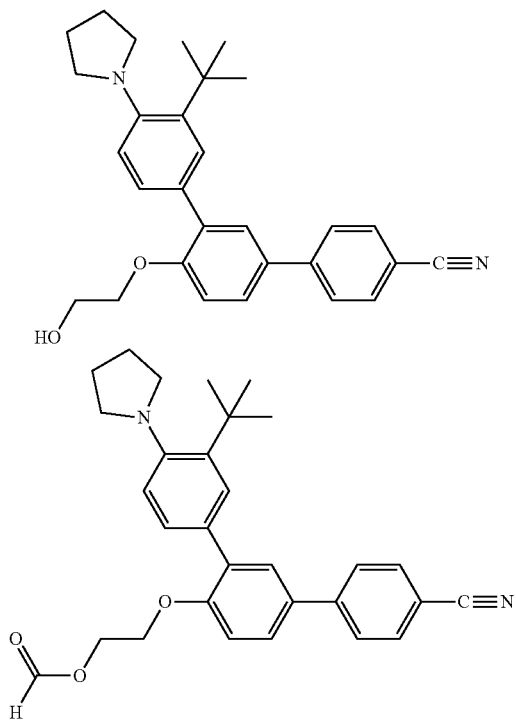

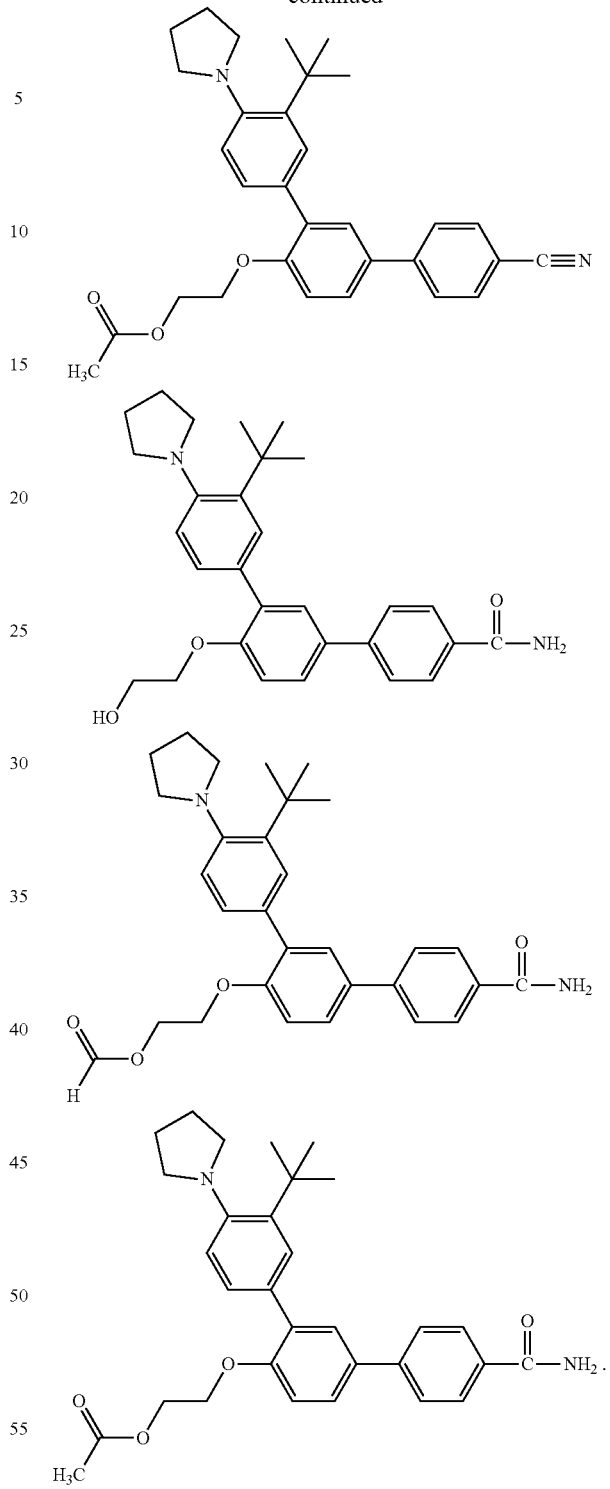

In some embodiments, the disclosure provides novel polymorphs of the compound of Formula (I), Trifarotene. The novel polymorphs described herein can be used to better characterize Trifarotene and its pharmaceutical properties.

Figure 2:
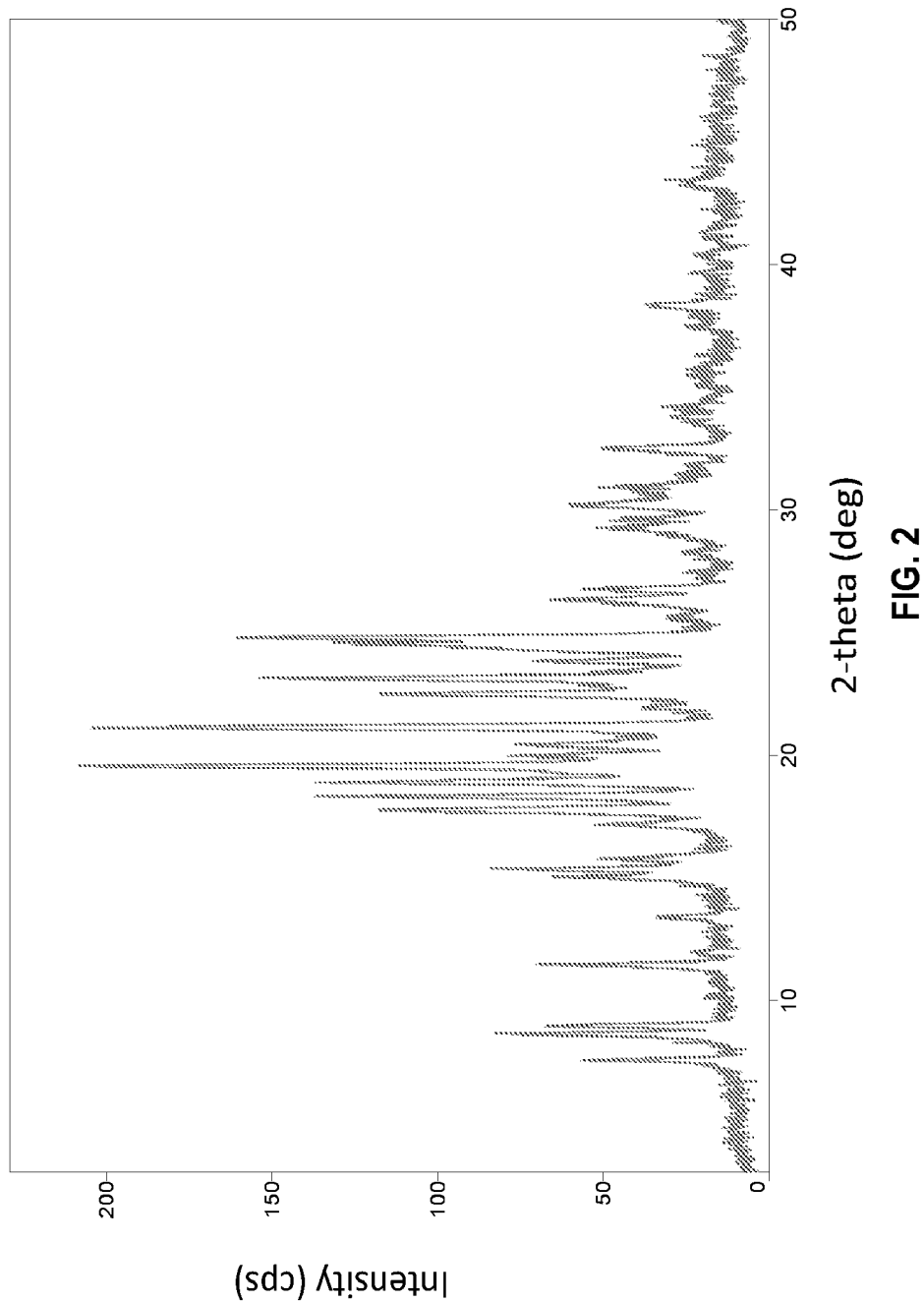
FIG. 2 shows an XRPD spectra of Trifarotene-HCl, Form A polymorph, as described in embodiments herein.

In some embodiments, the disclosure provides a Form A polymorph of the compound of Formula (I) [Trifarotene-HCl], wherein the Form A polymorph shows an X-ray powder diffraction (XRPD) pattern having characteristic peaks at reflection angle 2θ of 7.6, 11.5, 15.4, 21.1, and 23.2 degrees. In some embodiments, the Form A polymorph further shows peaks at peaks at 8.6, 9.0, 17.7, 18.3, 19.5, and 22.5 degrees. An exemplary XRPD spectra for the Form A polymorph is shown in FIG. 2.

In some embodiments, the disclosure further provides a process for preparing a Form A polymorph of Trifarotene-HCl, comprising: (a) providing trifarotene according to a process described herein; (b) adjusting pH of the trifarotene to a pH of about 2 to about 4, to obtain a trifarotene salt; and (c) suspending the trifarotene salt in methyl ethyl ketone, to obtain a Form A polymorph of trifarotene. In some embodiments, the pH is adjusted using an acid described herein. In some embodiments, the pH is adjusted using HCl.

Figure 3:
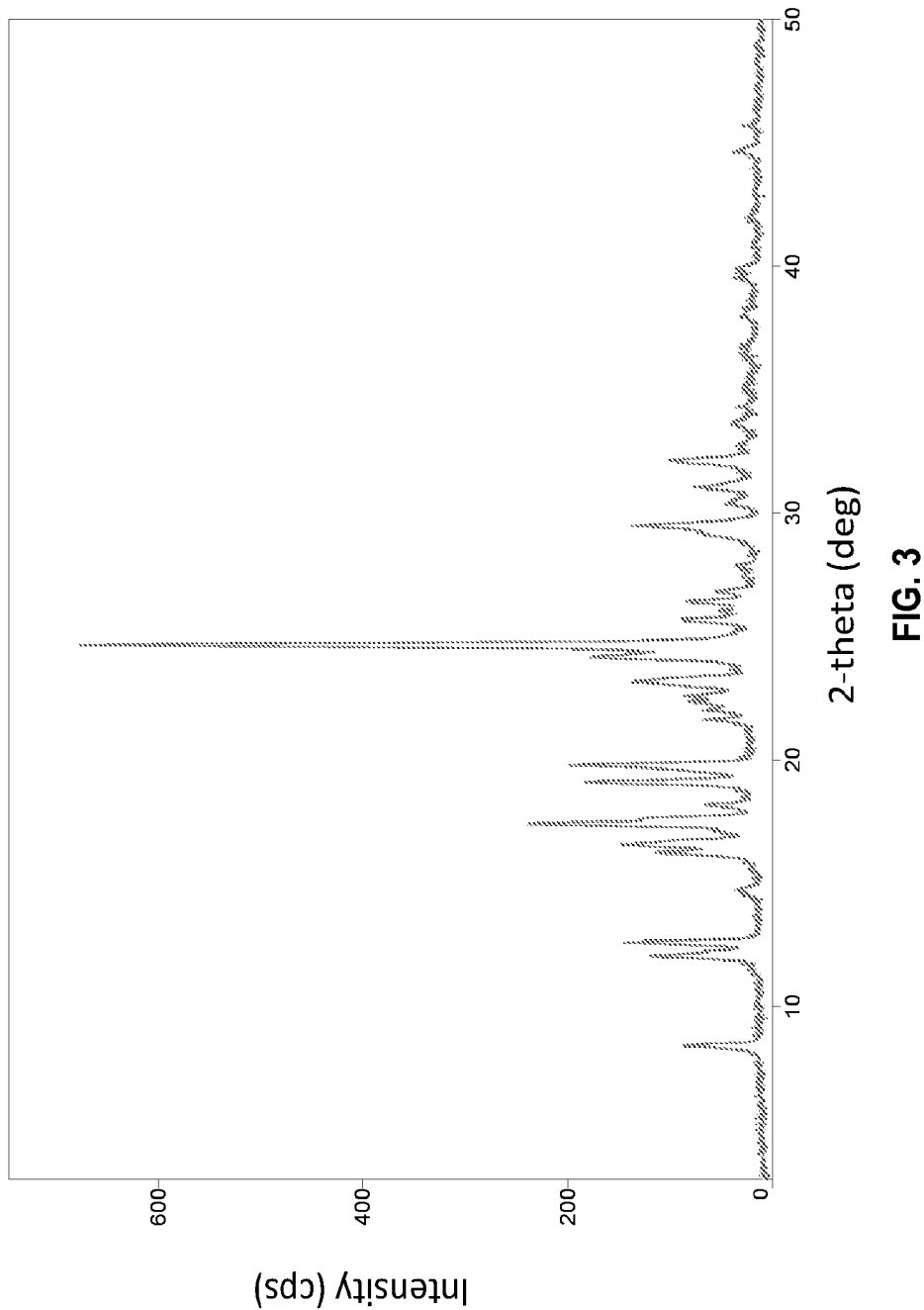
FIG. 3 shows an XRPD spectra of Trifarotene-HCl, Form B polymorph, as described in embodiments herein.

In some embodiments, the disclosure provides a Form B polymorph of the compound of Formula (I) [Trifarotene-HCl], wherein the Form B polymorph shows an X-ray powder diffraction pattern having characteristic peaks at reflection angle 2θ of 12.6, 19.5, 19.8, 24.6, and 29.5 degrees. In some embodiments, the Form B polymorph further shows peaks at 8.4, 12.0, 17.4, 21.1, 23.2, 31.0, and 32.1 degrees. An exemplary XRPD spectra for the Form B polymorph is shown in FIG. 3.

In some embodiments, the disclosure further provides a process for preparing a Form B polymorph of Trifarotene-HCl, comprising: (a) providing trifarotene according to a process described herein; (b) adjusting pH of the trifarotene to a pH of about 2 to about 4, to obtain a trifarotene salt; and (c) suspending the trifarotene salt in a solvent comprising acetonitrile, ethyl acetate, tetrahydrofuran, 1-butanol; or dissolving the trifarotene salt in methanol, to obtain a Form B polymorph of trifarotene. In some embodiments, the pH is adjusted using an acid described herein. In some embodiments, the pH is adjusted using HCl.

Figure 4:
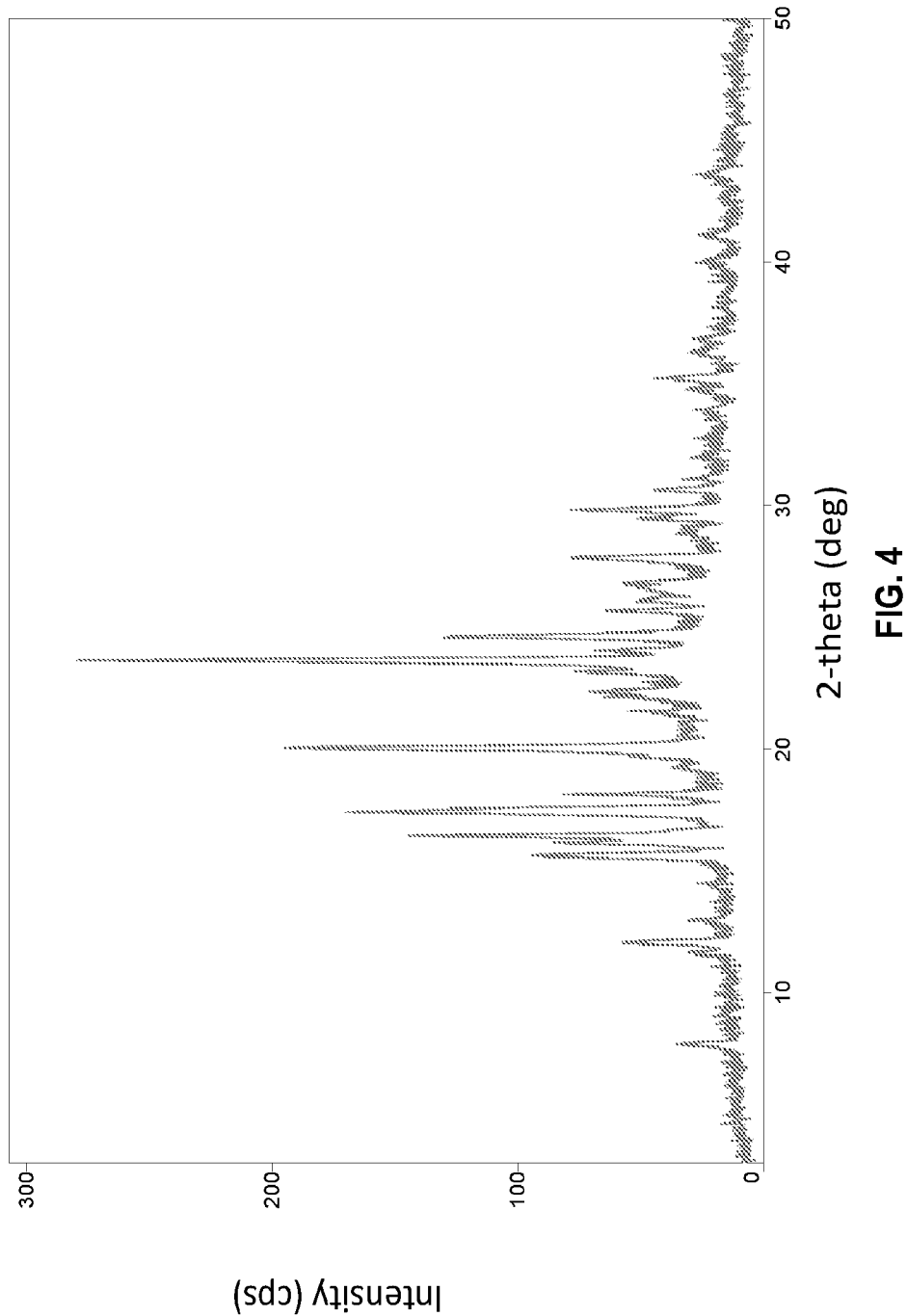
FIG. 4 shows an XRPD spectra of Trifarotene-HCl, Form C polymorph, as described in embodiments herein.

In some embodiments, the disclosure provides a Form C polymorph of the compound of Formula (I) [Trifarotene-HCl], wherein the Form C polymorph shows an X-ray powder diffraction pattern having characteristic peaks at reflection angle 2θ of 7.9, 15.6, 20.0, 23.6, and 27.8 degrees. In some embodiments, the Form C polymorph further shows peaks at 12.1, 16.4, 17.4, and 28.8 degrees. An exemplary XRPD spectra for the Form C polymorph is shown in FIG. 4.

In some embodiments, the disclosure further provides a process for preparing a Form C polymorph of Trifarotene-HCl, comprising: providing trifarotene according to a process described herein; (b) adjusting pH of the trifarotene to a pH of about 2 to about 4, to obtain a trifarotene salt; and (c) suspending the trifarotene salt in ethylene glycol, to obtain a Form C polymorph of trifarotene. In some embodiments, the pH is adjusted using an acid described herein. In some embodiments, the pH is adjusted using HCl.

Figure 5:
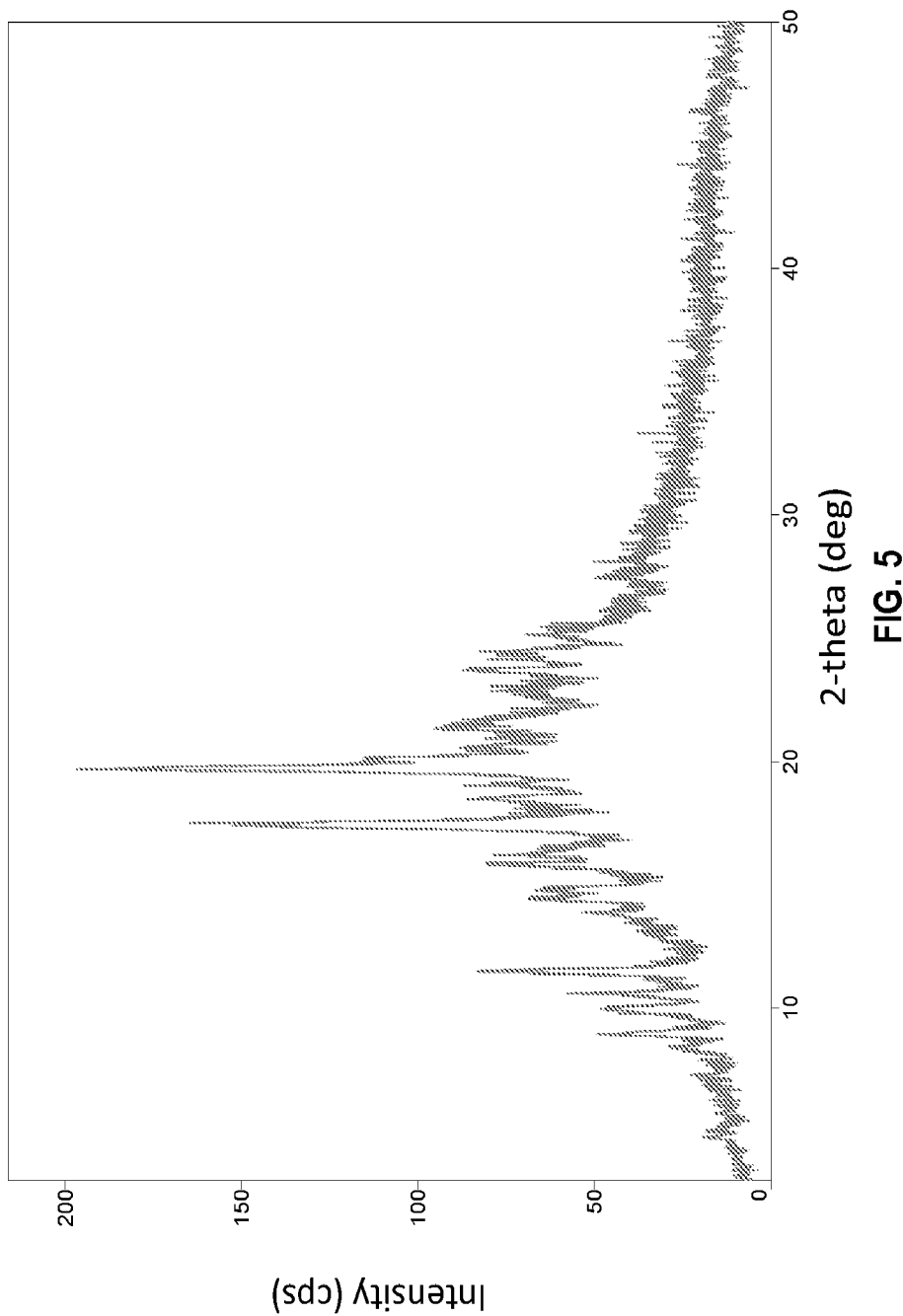
FIG. 5 shows an XRPD spectra of Trifarotene, Form D polymorph, as described in embodiments herein.

In some embodiments, the disclosure provides a Form D polymorph of the compound of Formula (I) [Trifarotene], wherein the Form D polymorph shows an X-ray powder diffraction pattern having characteristic peaks at reflection angle 2θ of 8.5, 16.2, 18.6, and 23.1 degrees. In some embodiments, the Form D polymorph further shows peaks at 12.2, 12.8, and 14.1 degrees. An exemplary XRPD spectra for the Form D polymorph is shown in FIG. 5.

In some embodiments, the disclosure further provides a process for preparing a Form D polymorph of Trifarotene, comprising: (a) providing trifarotene according to a process described herein; and (b) adjusting pH of the trifarotene to a pH of about 5 to about 6, to obtain a Form D polymorph of trifarotene. In some embodiments, the pH is adjusted using an acid described herein. In some embodiments, the pH is adjusted using HCl, acetic acid, sulfuric acid, phosphoric acid, nitric acid, hydrobromic acid, trifluoroacetic acid, p-toluene sulfonic acid, methane-sulfonic acid, or any mixture thereof.

Figure 6:
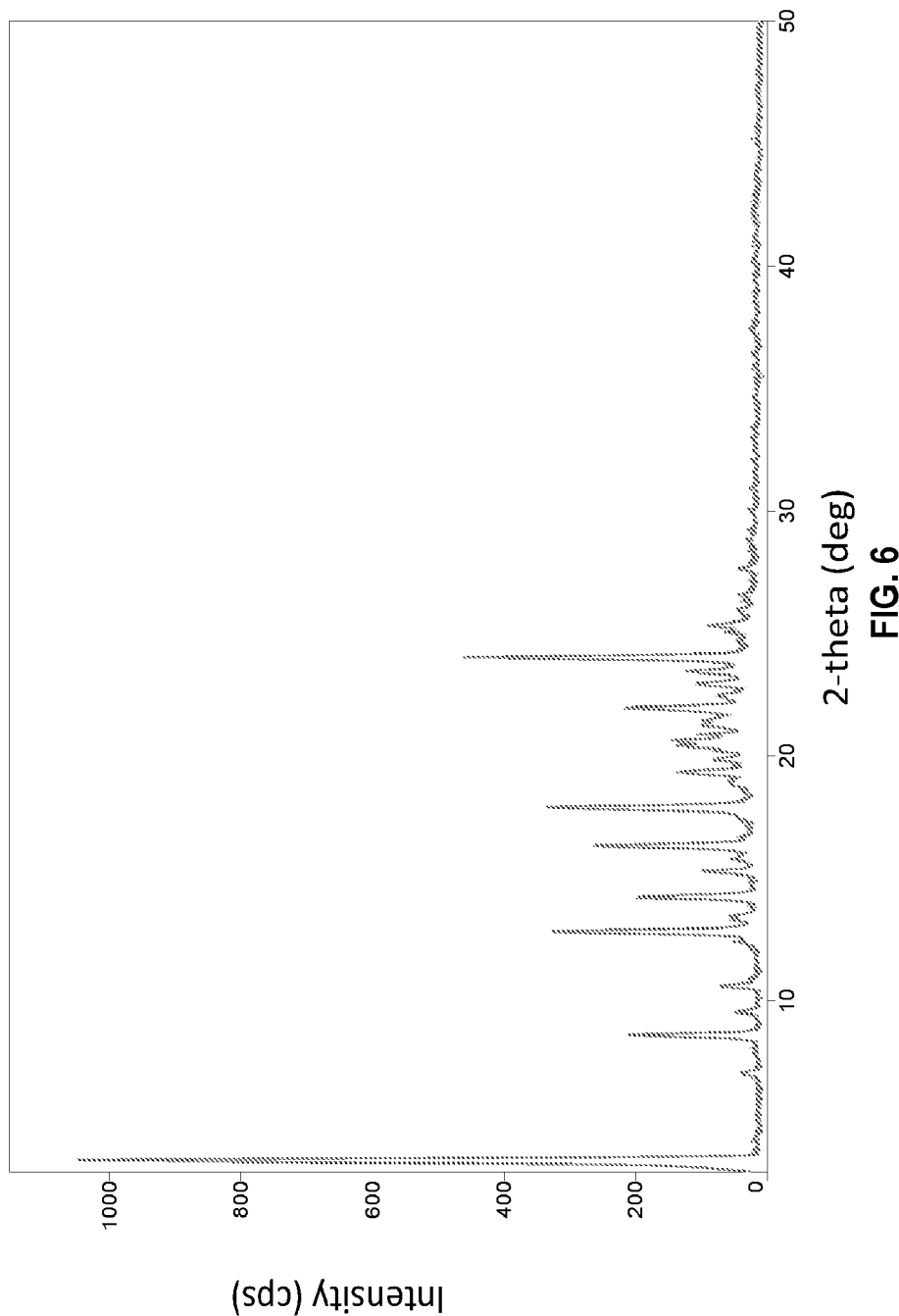
FIG. 6 shows an XRPD spectra of Trifarotene, Form E polymorph, as described in embodiments herein.

In some embodiments, the disclosure provides a Form E polymorph of the compound of Formula (I) [Trifarotene], wherein the Form E polymorph shows an X-ray powder diffraction pattern having characteristic peaks at reflection angle 2θ of 8.6, 12.8, 14.2, 17.9, and 24.0 degrees. In some embodiments, the Form E polymorph further shows peaks at 10.6, 15.3, 16.3, 19.3, and 22.0 degrees. An exemplary XRPD spectra for the Form E polymorph is shown in FIG. 6.

In some embodiments, the disclosure further provides a process for preparing a Form E polymorph of Trifarotene, comprising: (a) providing trifarotene according to a process described herein; (b) adjusting pH of the trifarotene to a pH of about 5 to about 6, to obtain trifarotene; and (c) suspending the trifarotene in methanol, to obtain a Form E polymorph of trifarotene.

Figure 7:
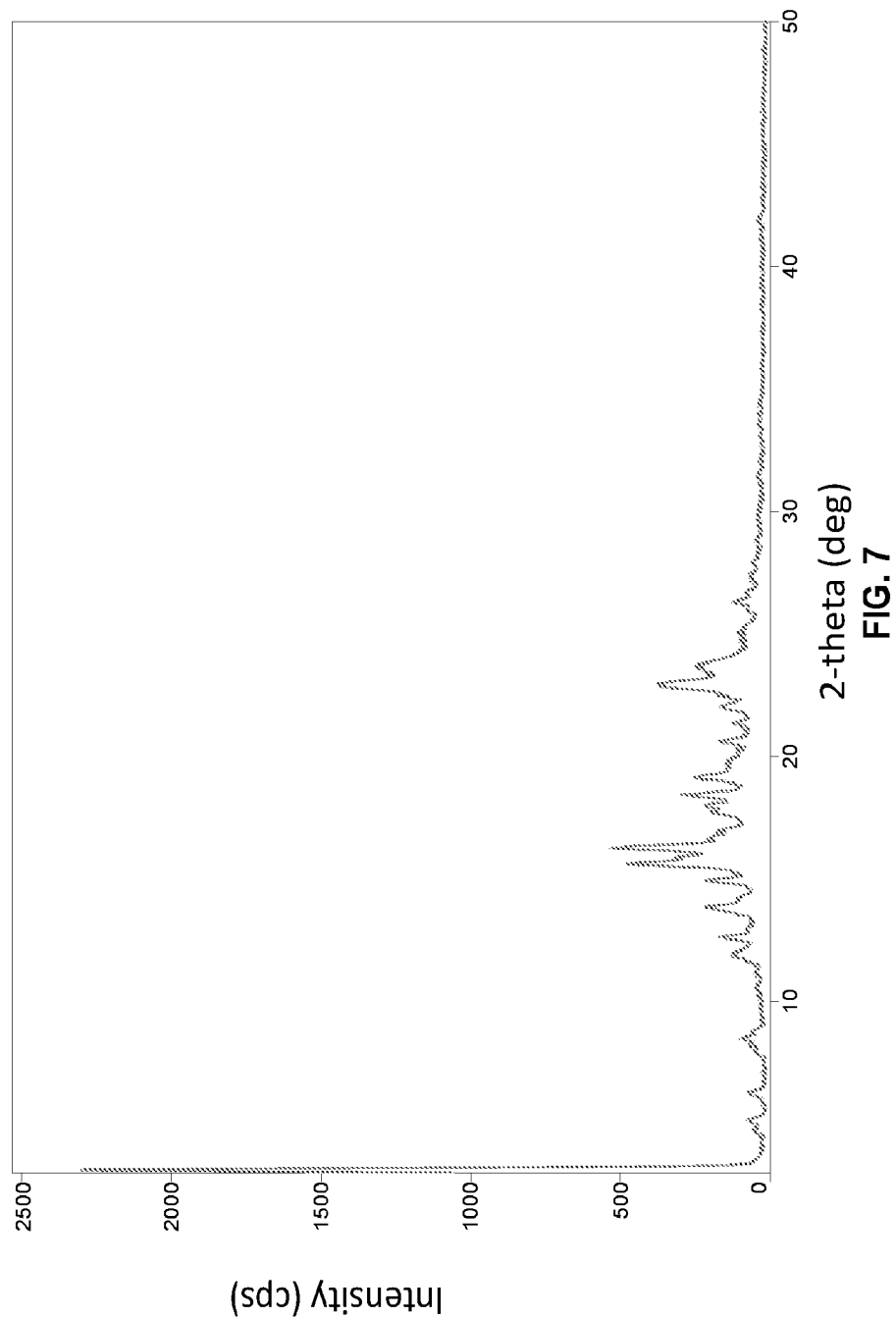
FIG. 7 shows an XRPD spectra of Trifarotene, Form F polymorph, as described in embodiments herein.

In some embodiments, the disclosure provides a Form F polymorph of the compound of Formula (I) [Trifarotene], wherein the Form F polymorph shows an X-ray powder diffraction pattern having characteristic peaks at reflection angle 2θ of 5.2, 6.3, 14.9, 18.0, and 19.1 degrees. In some embodiments, the Form F polymorph further shows peaks at 8.5, 15.6, 16.3, 18.5, and 22.9 degrees. An exemplary XRPD spectra for the Form F polymorph is shown in FIG. 7.

In some embodiments, the disclosure further provides a process for preparing a Form F polymorph of Trifarotene, comprising: (a) providing trifarotene according to a process described herein; (b) adjusting pH of the trifarotene to a pH of about 5 to about 6, to obtain trifarotene; and (c) dissolving the trifarotene in isopropanol, to obtain a Form F polymorph of trifarotene.

Figure 8:
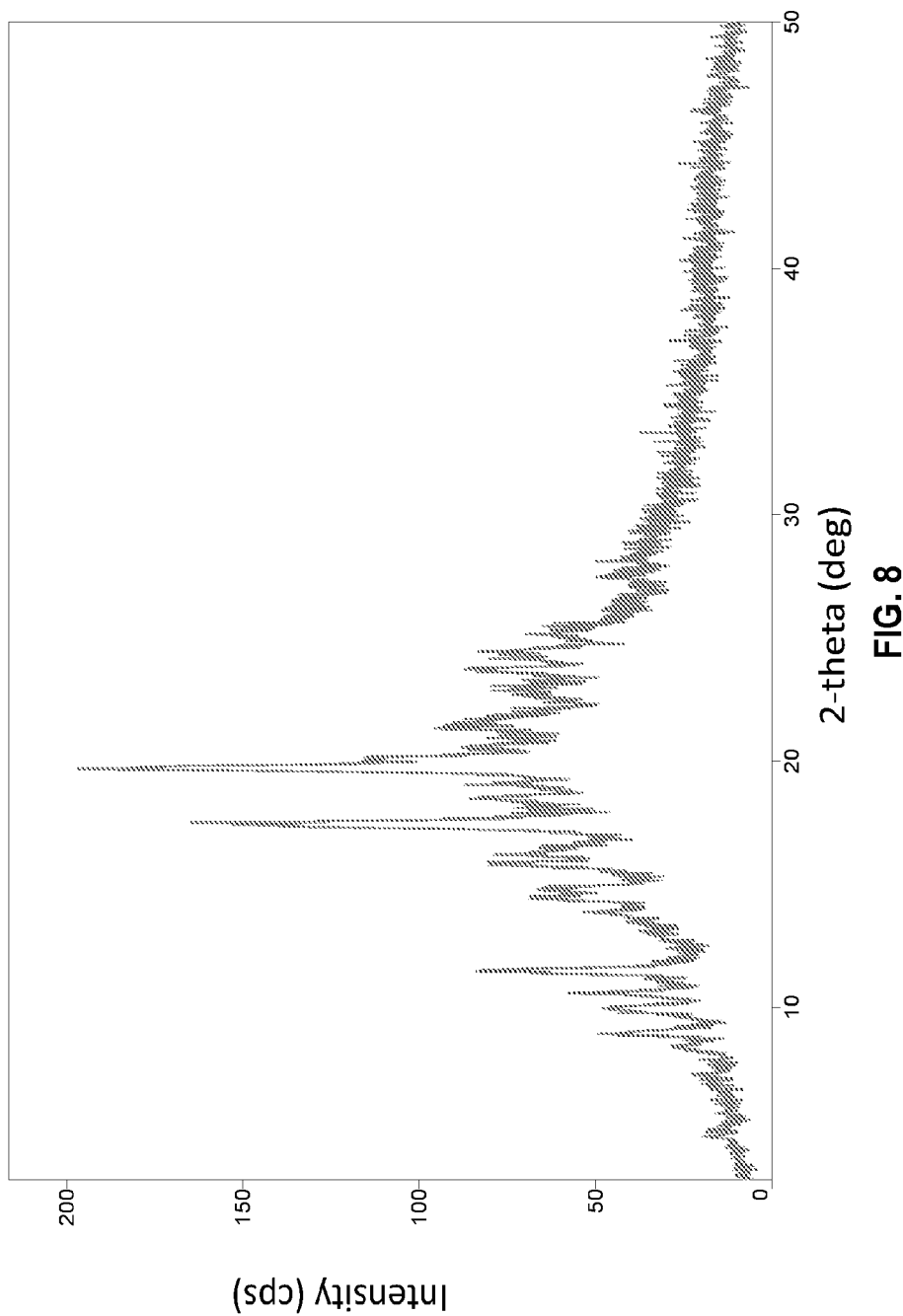
FIG. 8 shows an XRPD spectra of Trifarotene Na salt, Form G polymorph, as described in embodiments herein.

In some embodiments, the disclosure provides a Form G polymorph of the compound of Formula (I) [Trifarotene Na salt], wherein the Form G polymorph shows an X-ray powder diffraction pattern having characteristic peaks at reflection angle 2θ of 10.6, 11.5, 17.4, and 19.7 degrees. In some embodiments, the Form G polymorph further shows peaks at 8.9, 10.0, 14.7, and 16.2 degrees. An exemplary XRPD spectra for the Form G polymorph is shown in FIG. 8.

In some embodiments, the disclosure further provides a process for preparing a Form G polymorph of Trifarotene Na salt, comprising: (a) providing trifarotene according to a process of described herein; and (b) adjusting pH of the trifarotene to a pH of about 9 to about 12, to obtain a Form G polymorph of trifarotene salt. In some embodiments, the pH is adjusted using a base described herein. In some embodiments, the pH is adjusted using sodium hydroxide.

All references cited herein, including patents, patent applications, papers, textbooks and the like, and the references cited therein, to the extent that they are not already, are hereby incorporated herein by reference in their entirety.

EXAMPLES

Example 1. Synthesis of 3"-(tert-butyl)-4'-(2-hydroxyethoxy)-4"-(pyrrolidin-1-yl)-[1,1':3',1"-terphenyl]-4-carboxylic acid [Trifarotene]—One-Step Hydrolysis A. Preparation of 2-((3"-(tert-butyl)-4-cyano-4"-(pyrrolidin-1-yl)-[1,1':3',1"-terphenyl]-4'-yl)oxy) ethyl acetate [Formula IV(a)]

To 100 g (0.3 mol) of (3-(tert-butyl)-4-(pyrrolidin-1-yl) phenyl) boronic acid [Formula II] were added Toluene (1450 mL) and 85 g (0.21 mol) of 2-((4'-cyano-3-iodo-[1,1'-biphenyl]-4-yl)oxy)ethyl Acetate [Formula III]. 5M potassium carbonate (300 mL) was added. The reaction medium is stirred at 40° C. for 30 minutes under nitrogen. 0.87 g of Pd-100 (Palladium chloride bis(triphenylphosphine) (0.0013 mol) was added under nitrogen, and the reaction medium was heated to 85-90° C. and stirred under reflux for 6 hours. The reaction was terminated by the addition of water (625 mL). Phases were separated. The organic phase was filtered off. Toluene was distilled off in vacuum to afford oily residue.

The residue was suspended in heptane (3000 mL) and stirred under reflux for 1 hour and hot filtered off. The mother liquor was further heated under reflux for 1 hour and cooled gradually to room temperature. The precipitate was filtered off to afford 2-((3"-(tert-butyl)-4-cyano-4"-(pyrrolidin-1-yl)-[1,1':3',1"-terphenyl]-4'-yl)oxy)ethyl acetate [Formula IV(a)] which was further suspended in ethanol (150 ml) and heated under reflux for 2.5 hours followed by cooling to room temperature. The precipitate was filtered off to afford 50.0 g of 2-((3"-(tert-butyl)-4-cyano-4"-(pyrrolidin-1-yl)-[1,1':3',1"-terphenyl]-4'-yl)oxy)ethyl acetate [Formula IV(a)] as a white powder with HPLC purity 99.8%; yield 49%; m/z 483.26.

[Formula IV(a)]

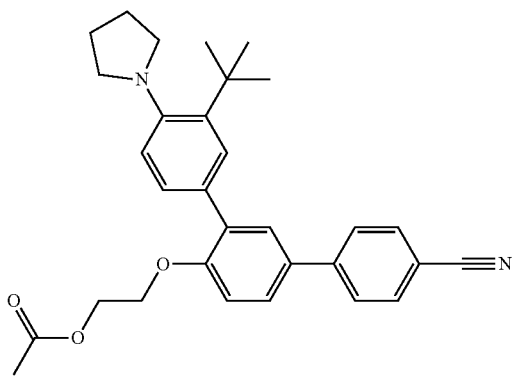

B. Synthesis of 3"-(tert-butyl)-4'-(2-hydroxyethoxy)-4"-(pyrrolidin-1-yl)-[1,1':3',1"-terphenyl]-4-carboxylic acid [Trifarotene; Formula I] from Formula IV(a)

To 50 g (0.104 mol) of 2-((3"-(tert-butyl)-4-cyano-4"-(pyrrolidin-1-yl)-[1,1':3',1"-terphenyl]-4'-yl)oxy)ethyl acetate [Formula IV(a)] were added 5M NaOH solution (100 mL) and ethanol (200 mL). The reaction medium was stirred under reflux for 15 hours. The reaction medium was cooled to 40° C., and water (400 mL) was added. HCl 32% (50 mL) was added dropwise to pH 5.5. The white precipitate was filtered off to afford crude 3"-(tert-butyl)-4'-(2-hydroxyethoxy)-4"-(pyrrolidin-1-yl)-[1,1':3',1"-terphenyl]-4-carboxylic acid, which was suspended in ethanol (40 ml) and water (40 ml). The mixture was heated to 40° C. for 5 hours and filtered off to afford 39.5 g 3"-(tert-butyl)-4'-(2-hydroxyethoxy)-4"-(pyrrolidin-1-yl)-[1,1':3',1"-terphenyl]-4-carboxylic acid pure [Trifarotene; Formula I] with HPLC purity 99.9%; yield 74%; m/z 460.24.

[Formula I]

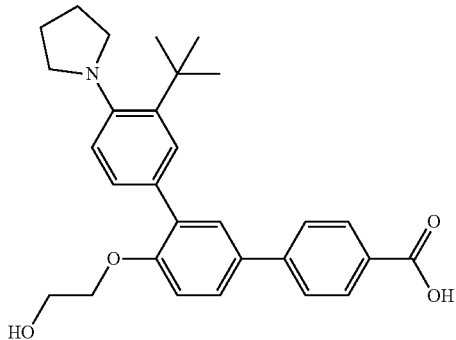

Example 2. Synthesis of 3"-(tert-butyl)-4'-(2-hydroxyethoxy)-4"-(pyrrolidin-1-yl)-[1,1':3',1"-terphenyl]-4-carboxylic acid [Trifarotene]—Two-Step Hydrolysis A. The Compound of Formula IV(a) was Prepared According to Example 1.A B. Preparation of 3"-(tert-butyl)-4'-(2-hydroxyethoxy)-4"-(pyrrolidin-1-yl)-[1,1':3',1"-terphenyl]-4-carbonitrile [Formula V(a)]

2.0 g (0.004 mol) of 2-((3"-(tert-butyl)-4-cyano-4"-(pyrrolidin-1-yl)-[1,1':3',1"-terphenyl]-4'-yl)oxy)ethyl acetate [Formula IV(a)] was suspended in ethanol (60 ml). 2.9 g (0.021 mol) of potassium carbonate was added. The reaction medium is stirred at 25° C. for 2.5 hours, followed by reflux for two hours and filtered hot. The solution was concentrated to 20 mL, cooled gradually to room temperature and stirred for 15-18 hours to afford white precipitate that was filtered off to obtain an off-white to beige solid; purity 90.75%; yield 97.2% (based on dry). The product was stirred under reflux in heptane (30 mL) for 15-18 hours, then gradually cooled to 10-15° C. Stirring was continued for 1 hour. The obtained precipitate [Formula V(a)] was filtered off to afford an off-white to slightly beige solid with purity 97.9%; yield 96%; m/z 441.26.

[Formula V(a)]

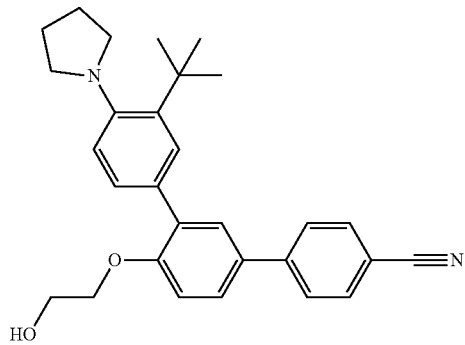

C. Synthesis of 3"-(tert-butyl)-4'-(2-hydroxyethoxy)-4"-(pyrrolidin-1-yl)-[1,1':3',1"-terphenyl]-4-carboxylic acid [Trifarotene; Formula I] from Formula V(a)

11.0 g (0.025 mol) of 3"-(tert-butyl)-4'-(2-hydroxyethoxy)-4"-(pyrrolidin-1-yl)-[1,1':3',1"-terphenyl]-4-carbonitrile was suspended in 0.5 M NaOH:EtOH solution (25:50 mL). The suspension was heated under reflux for 18-22 hours and converted into a dark yellow solution. The reaction medium was cooled to room temperature, diluted with water (82 mL), acidified with HCl 32% to pH=4.7 and stirred at room temperature for 2 hours. The formed precipitate was filtered off, washed with an ethanol:water 20:80 mixture, and dried under vacuum at 45° C. to afford a Trifarotene [Formula I] as a white powder with purity 99.5%; m/z 460.24.

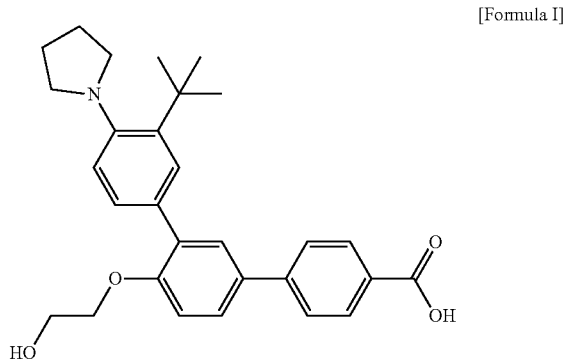 [SMILES: CC(C)(C)c1cc(-c2cc(-c3ccc(C(=O)O)cc3)ccc2OCCO)ccc1N1CCCC1]

[Formula I]

Example 3. Preparation of 2-((4'-cyano-3-iodo-[1,1'-biphenyl]-4-yl)oxy)ethyl acetate [Formula III(a)]

To 180 g (0.56 mol) of 4'-hydroxy-3'-iodo-biphenyl-4-carbonitrile were added dimethylformamide (900 mL) and 247 g (1.8 mol) of potassium carbonate. The reaction medium was stirred at 25° C. for 30 min. 117 g (0.7 mol) of 2-bromoethyl acetate was added, and the reaction medium was heated to 60-65° C. and stirred for 6 hours. The reaction was terminated by the addition of water (1800 mL). The reaction medium was cooled to 25° C. The precipitate was filtered off to afford 213.5 g of [Formula III(a)]; 90.6% yield; HPLC purity 97%.

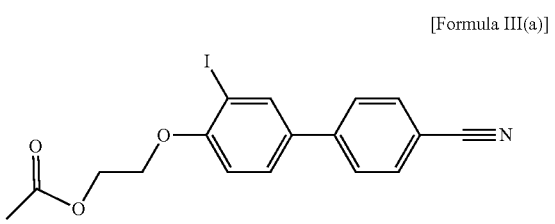 [SMILES: CC(=O)OCCOc1ccc(-c2ccc(C#N)cc2)cc1I]

[Formula III(a)]

Example 4. Preparation of (3-(tert-butyl)-4-(pyrrolidin-1-yl)phenyl) boronic acid [Formula II(a)]

40.0 g (0.14 mol) of 1-(4-bromo-2tert-butyl) phenyl) pyrrolidine, 34.8 g (0.355 mol) of potassium acetate anhydrous, 0.15 g (2.8×10⁻⁴ mol) of Pd-168, 400 mL ethanol (EtOH) and 120 mL ethylene glycol under nitrogen atmosphere were mixed together. 25.5 g (0.282 mol) of tetrahydroxyborane was added with agitation in one portion. After 5 minutes, the temperature rose up to 35-45° C. Reaction mixture was stirred at 40° C. for 4-5 hours. A dark brown/grey suspension formed. The reaction was terminated by adding 500 mL water at temperature below 25° C. The reaction mixture was stirred at 20-25° C. for 2-3 hours. The solid was filtered off and washed with 500 mL water to afford 31.5 g of (3-(tert-butyl)-4-(pyrrolidin-1-yl)phenyl) boronic acid [Formula II(a)]; purity 98.3%.

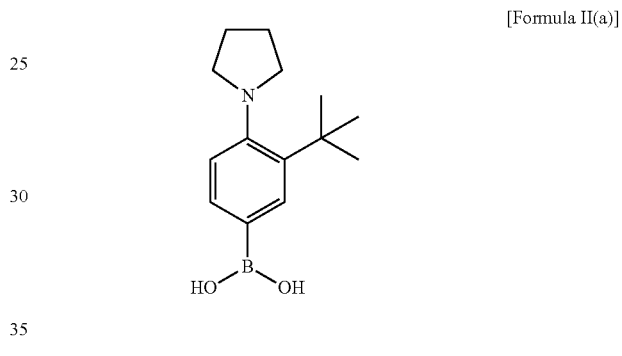

[Formula II(a)]

Example 5. Alternative Method for Preparation of 2-((3"-(tert-butyl)-4-cyano-4"-(pyrrolidin-1-yl)-[1,1':3',1"-terphenyl]-4'-yl)oxy)ethyl acetate [Formula IV(a)]

To 247 g (0.015 mol) of (3-(tert-butyl)-4-(pyrrolidin-1-yl)phenyl) boronic acid were added dimethylacetamide (1000 mL) and 100 g (0.25 mol) of 2-((4'-cyano-3-iodo-[1,1'-biphenyl]-4-yl)oxy)ethyl acetate. 1.5 M potassium phosphate tribasic (500 mL) was added. The reaction medium is stirred for 15 minutes under nitrogen. 1.66 g (0.0074 mol) of palladium acetate was added under nitrogen, and the reaction medium was stirred for 3 hours at 25° C. The reaction was terminated by the addition of water (500 mL). The precipitate was filtered off.

The solid was suspended in heptane (2500 mL) and stirred under reflux for 1 hour and hot filtered off. The mother liquor was further heated under reflux for 1 hour and cooled gradually to room temperature. The precipitate was filtered off to afford 2-((3"-(tert-butyl)-4-cyano-4"-(pyrrolidin-1-yl)-[1,1':3',1"-terphenyl]-4'-yl)oxy)ethyl acetate, which was further suspended in ethanol (150 mL) and heated under reflux for 2.5 hours followed by cooling to room temperature. The precipitate was filtered off to afford 50.0 g of 2-((3"-(tert-butyl)-4-cyano-4"-(pyrrolidin-1-yl)-[1,1':3',1"-terphenyl]-4'-yl)oxy)ethyl acetate as a white powder with HPLC purity 99.6%; yield 54%; m/z 483.26.

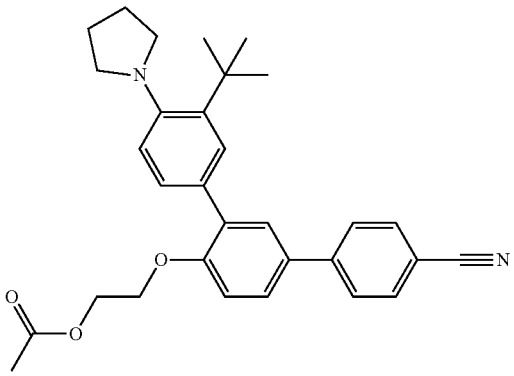

[Formula IV(a)]

Example 6. Preparation of Trifarotene HCl Salt 2-((3"-(tert-butyl)-4-cyano-4"-(pyrrolidin-1-yl)-[1,1':3',1"-terphenyl]-4'-yl)oxy)ethyl acetate (11 g) in a mixture of EtOH:20% NaOH aq. solution (50 mL:25 mL) was heated under reflux for 18 hours. The reaction mixture was cooled to room temperature and acidified to pH 2 with HCl 32%. The mixture was stirred at room temperature for 2 hours, filtered off, and the cake was washed with EtOH:H$_2$O 20:80 (100 mL). Trifarotene HCl salt was dried under vacuum at 40-45° C. to afford 11.0 g of Trifarotene HCl. The XRPD of the resulting sample is shown in FIG. 1.

Example 7. Preparations of Trifarotene HCl—Form B Polymorph

A. 150 mg of Trifarotene HCl salt obtained in Example 6 was suspended in acetonitrile (5 mL) and shaken at 300 rpm for 3 days at room temperature. The product was filtered off and dried under ambient conditions. The resulting crystal form is the Form B polymorph as determined by XRPD. The XRPD of a Form B polymorph is shown in FIG. 3.

B. 150 mg of Trifarotene HCl salt obtained in Example 6 was suspended in ethyl acetate (5 mL) and shaken at 300 rpm for 3 days at room temperature. The product was filtered off and dried under ambient conditions. The resulting crystal form is the Form B polymorph as determined by XRPD.

C. 150 mg of Trifarotene HCl salt obtained in Example 6 was suspended in tetrahydrofuran (5 mL) and shaken at 300 rpm for 3 days at room temperature. The product was filtered off and dried under ambient conditions. The resulting crystal form is the Form B polymorph as determined by XRPD.

D. 150 mg of Trifarotene HCl salt obtained in Example 6 was suspended in 1-butanol (5 mL) and shaken at 300 rpm for 3 days at room temperature. The product was filtered off and dried under ambient conditions. The resulting crystal form is the Form B polymorph as determined by XRPD.

Example 8. Alternative Preparation of Trifarotene HCl—Form B Polymorph 1.5 g Trifarotene HCl salt obtained in Example 6 was dissolved under reflux in MeOH (33 mL). The turbid solution was filtered off through glass filter paper. The solution was left for evaporation at room temperature for 3 days. The product was filtered off and washed with cold MeOH (3 mL). The product was dried under ambient conditions. The resulting crystal form is the Form B polymorph as determined by XRPD.

Example 9. Preparation of Trifarotene HCl—Form A Polymorph 150 mg Trifarotene HCl salt obtained in Example 6 was suspended in methyl ethyl ketone (5 mL) and shaken at 300 rpm for 3 days at room temperature. The product was filtered off and dried under ambient conditions. The resulting crystal form is the Form A polymorph as determined by XRPD. The XRPD of a Form A polymorph is shown in FIG. 2.

Example 10. Preparation of Trifarotene HCl—Form C Polymorph 150 mg Trifarotene HCl salt obtained in Example 6 was suspended in ethylene glycol (5 mL) and shaken at 300 rpm for 3 days at room temperature. The product was filtered off and dried under ambient conditions. The resulting crystal form is the Form C polymorph as determined by XRPD. The XRPD of a Form C polymorph is shown in FIG. 4.

Example 11. Preparation of Trifarotene—Form D Polymorph 2-((3"-(tert-butyl)-4-cyano-4"-(pyrrolidin-1-yl)-[1,1':3',1"-terphenyl]-4'-yl)oxy)ethyl acetate (5 g) in a mixture of EtOH:20% NaOH aq. solution (22 mL:11 mL) was heated under reflux for 18 hours. The reaction mixture was cooled to room temperature and acidified to pH 5.5 with HCl 32%. The mixture was stirred at room temperature for 2 hours, filtered off, and the cake was washed with EtOH:H2O 20:80 (45 mL). Trifarotene was dried under vacuum at 40-45° C. for 12-48 hours (18 hours) to afford 4.6 g of Trifarotene. The resulting crystal form is the Form D polymorph as determined by XRPD. The XRPD of the Form D polymorph is shown in FIG. 5.

Example 12. Preparation of Trifarotene—Form E Polymorph 150 mg Trifarotene obtained in Example 11 was suspended in MeOH (5 mL) and shaken at 300 rpm for 2 days at room temperature. The product was filtered off and dried under ambient conditions for 2-6 days (3 days). The resulting crystal form is the Form E polymorph as determined by XRPD. The XRPD of the Form E polymorph is shown in FIG. 6.

Example 13. Preparation of Trifarotene—Form F Polymorph 1.5 g Trifarotene obtained in Example 11 was dissolved under reflux in IPA (24 mL). The turbid solution was filtered off through nylon filter paper. The solution was left for evaporation at room temperature for 3 days. The product was filtered off and washed with cold IPA (1.5 mL). The product was dried under ambient conditions for 2-6 days (3 days). The resulting crystal form is the Form F polymorph as determined by XRPD. The XRPD of the Form F polymorph is shown in FIG. 7.

Example 14. Preparation of Trifarotene—Form G Polymorph 4.59 g of Trifarotene Form A obtained according to Example 9 was suspended in MeOH:H$_2$O 1:1 (400 mL). 0.1

N NaOH was added dropwise with pH control, up to pH 11.5. The mixture was stirred at room temperature for 30 minutes, and the precipitate was filtered off. The cake was washed with water (20 mL). Trifarotene sodium salt was dried under vacuum at 40-45° C. for 12-48 hours (18 hours) to afford 4.3 g of Trifarotene sodium salt. The resulting crystal form is the Form G polymorph as determined by XRPD. The XRPD of the Form G polymorph is shown in FIG. 8.

What is claimed is:

1. A process for the preparation of a compound of formula (I) [Trifarotene], or a salt thereof

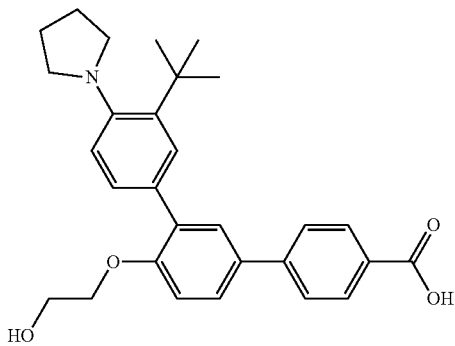

(I)

comprising hydrolyzing a compound of formula (V)

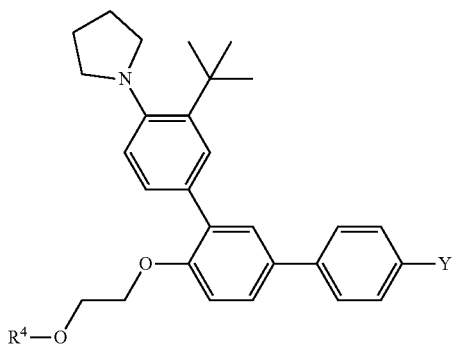

(V)

wherein $R^4$ is hydrogen, a substituted or unsubstituted linear or branched $C_1$-$C_8$ alkanoyl group, a substituted or unsubstituted linear or branched $C_2$-$C_8$ alkenoyl group, a substituted or unsubstituted linear or branched $C_2$-$C_8$ alkynoyl group, a substituted or unsubstituted cycloalkanoyl group, a substituted or unsubstituted aryl carbonyl group, a substituted or unsubstituted heterocyle carbonyl group, a substituted or unsubstituted heteroaryl carbonyl group, or a $C_1$-$C_8$ alkanoyl group wherein one or more carbons in the $C_1$-$C_8$ alkanoyl group is replaced by one or more heteroatoms; and
wherein Y is a nitrile (CN) or amide ($CONH_2$);
to obtain the compound of formula (I).

2. The process according to claim 1, wherein $R^4$ is an acetyl group, or wherein $R^4$ is hydrogen.

3. The process according to claim 1, further comprising preparing the compound of formula (V) by hydrolyzing a compound of Formula (IV)

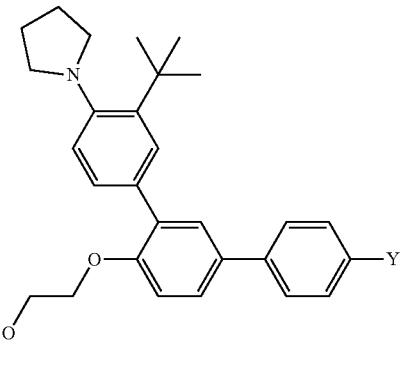

(IV)

in the presence of a solvent comprising a base,
wherein $R^3$ is hydrogen, a hydroxyl group, a halogen, a substituted or unsubstituted linear or branched $C_1$-$C_8$ alkyl group, a substituted or unsubstituted linear or branched $C_2$-$C_8$ alkenyl group, a substituted or unsubstituted linear or branched $C_2$-$C_8$ alkynyl group, a substituted or unsubstituted cycloalkyl group, a substituted or unsubstituted aryl group, a substituted or unsubstituted heterocycle, a substituted or unsubstituted heteroaryl, or a $C_1$-$C_8$ alkyl group wherein one or more carbons in the $C_1$-$C_8$ alkyl group is replaced by one or more heteroatoms; and
wherein Y is a nitrile (CN) or amide ($CONH_2$);
to obtain the compound of formula (V).

4. The process according to claim 3, wherein $R^3$ is methyl.

5. The process according to claim 1, wherein the hydrolysis is performed in the presence of a solvent comprising water, methanol (MeOH), ethanol (EtOH), propanol (PrOH), isopropanol (IPA), or any mixture thereof.

6. The process according to claim 3, wherein the base comprises sodium hydroxide (NaOH), potassium hydroxide (KOH), lithium hydroxide (LiOH), barium hydroxide (Ba(OH)$_2$), or any mixture thereof.

7. The process according to claim 3, wherein the compound of formula (IV) is present in an amount of about 0.01 to about 0.5 mol/L (solvent).

8. The process according to claim 3, wherein the base is present in an amount of about 0.1 to about 1 mol/L (solvent).

9. The process according to claim 8, wherein the base is present at about 1 to about 10 molar equivalents relative to the compound of formula (IV).

10. The process according to claim 3, further comprising preparing the compound of formula (IV) by reacting a compound of formula (II)

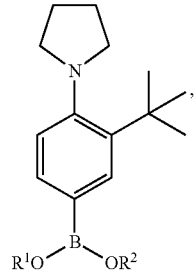

(II)

wherein $R^1$ and $R^2$ are independently hydrogen or a linear or branched $C_1$-$C_3$ alkyl, wherein $R^1$ and $R^2$ can be the same or different; or $R^1$ and $R^2$ together form a pinacolate,
with a compound of formula (III)

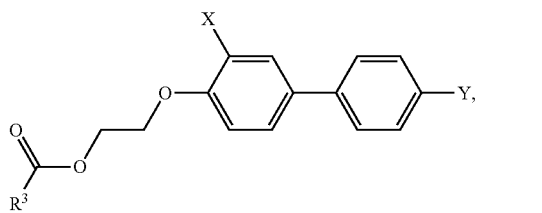

(III)

in the presence of a catalyst,
wherein $R^3$ is hydrogen, a hydroxyl group, a halogen, a substituted or unsubstituted linear or branched $C_1$-$C_8$ alkyl, a substituted or unsubstituted linear or branched $C_2$-$C_8$ alkenyl group, a substituted or unsubstituted linear or branched $C_2$-$C_8$ alkynyl group, a substituted or unsubstituted cycloalkyl group, a substituted or unsubstituted aryl group, a substituted or unsubstituted heterocycle, a substituted or unsubstituted heteroaryl, or a substituted or unsubstituted $C_1$-$C_8$ alkyl group wherein one or more carbons in the $C_1$-$C_8$ alkyl group is replaced by one or more heteroatoms;
wherein X is a halogen or triflate; and
wherein Y is a nitrile or amide,
to obtain the compound of formula (IV).

11. The process according to claim 10, wherein the $R^3$ is methyl and X is iodine.

12. The process according to claim 10, wherein the reaction is performed in the presence of a solvent comprising toluene, dimethylformamide (DMF), dimethyl sulfoxide (DMSO), tetrahydrofuran (THF), dioxane, n-butanol (n-BuOH), isopropanol (IPA), dimethyl ether (DME), diethyl ether, or any mixture thereof.

13. The process according to claim 10, wherein the reaction is performed in the presence of a base comprising $K_2CO_3$, $CH_3CO_2K$, $K_3PO_4$, KOtBu, $Na_2CO_3$, $NaHCO_3$, NaOMe, $Cs_2CO_3$, $Ag_3PO_4$, $Ag_2O$, $Tl_2CO_3$, TlOEt, TlOH, t-$BuNH_2$, KOH, NaOH, LiOH, $Ba(OH)_2$, or combination thereof.

14. The process according to claim 10, wherein the catalyst comprises a metal selected from Pd, Cu, or Ni.

15. The process according to claim 14, wherein the catalyst comprises at least two atoms of the metal.

16. The process according to claim 14, wherein the catalyst is a Pd catalyst selected from:
Pd(PPh$_3$)$_2$Cl$_2$ [Bis(triphenylphosphine)palladium(II) dichloride];
Pd(PPh$_3$)$_4$ [Tetrakis(triphenylphosphine)palladium(0)];
Pd(OAc)$_2$ [Palladium (II) diacetate];
XPhos Pd-G3 [(2-Dicyclohexylphosphino-2',4',6'-triisopropyl-1,1'-biphenyl)[2-(2'-amino-1,1'-biphenyl)]palladium(II) Methanesulfonate];
SPhos-Pd-G2 [Chloro(2-dicyclohexylphosphino-2',6'-dimethoxy-1,1'-biphenyl)[2-(2'-amino-1,1'-biphenyl)]palladium(I)];
A Pd-G3 [Mesylate[(di(1-adamantyl)-n-butylphosphine)-2-(2'-amino-1,1'-biphenyl)]palladium(II), [(Di(1-adamantyl)-butylphosphine)-2-(2'-amino-1,1'-biphenyl)]palladium(II) Methanesulfonate];
APhos-Pd-G3 [Palladium G3-(4-(N,N-Dimethylamino)phenyl)di-tert-butylphosphine, [4-(Di-tert-butylphosphino)-N,N-dimethylaniline-2-(2'-aminobiphenyl)]palladium(II) Methanesulfonate];
P(Cy$_3$) Pd-G3 [(Tricyclohexylphosphine)-2-(2'-aminobiphenyl)]palladium(II) Methanesulfonate];
Allylpalladium(II) chloride dimer Bis(allyl)dichlorodipalladium; or
Pd(dppf)Cl$_2$ [1,1'-Bis(diphenylphosphino)ferrocene]dichloropalladium(II)].

17. A compound of formula (V)

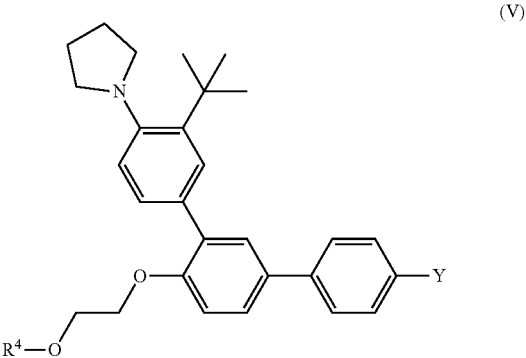

(V)

wherein $R^4$ is hydrogen, a substituted or unsubstituted linear or branched $C_1$-$C_8$ alkanoyl group, a substituted or unsubstituted linear or branched $C_2$-$C_8$ alkenoyl group, a substituted or unsubstituted linear or branched $C_2$-$C_8$ alkynoyl group, a substituted or unsubstituted cycloalkanoyl group, a substituted or unsubstituted aryl carbonyl group, a substitute or unsubstituted heterocyle carbonyl group, a substituted or unsubstituted heteroaryl carbonyl group, or a $C_1$-$C_8$ alkanoyl group wherein one or more carbons in the $C_1$-$C_8$ alkanoyl group is replaced by one or more heteroatoms; and
wherein Y is a nitrile (CN) or amide (CONH$_2$).

18. The compound of claim 17, wherein $R^4$ is hydrogen.

19. The compound according to claim 17, wherein $R^4$ is acetyl.

20. A process for preparing a Form E polymorph of trifarotene, comprising:
a. providing trifarotene according to the process of claim 1;
b. adjusting pH of the trifarotene to a pH of about 5 to about 6, to obtain trifarotene; and
c. suspending the trifarotene in methanol, to obtain a Form E polymorph of Trifarotene.

* * * * *